(12) United States Patent
Kornerup et al.

(10) Patent No.: US 7,985,199 B2
(45) Date of Patent: Jul. 26, 2011

(54) GATEWAY SYSTEM

(75) Inventors: Grete Kornerup, Vipperød (DK); Lasse W. Mogensen, Søborg (DK); Jens E. Nielsen, Ringsted (DK); Orla Mathiasen, Sorø (DK)

(73) Assignee: Unomedical A/S, Birkeroed (DK)

( * ) Notice: Subject to any disclaimer, the term of this patent is extended or adjusted under 35 U.S.C. 154(b) by 627 days.

(21) Appl. No.: 11/908,776

(22) Filed: Apr. 17, 2008

(65) Prior Publication Data

US 2008/0215003 A1    Sep. 4, 2008

Related U.S. Application Data

(63) Continuation of application No. PCT/DK2006/050005, filed on Feb. 23, 2006.

(60) Provisional application No. 60/662,667, filed on Mar. 17, 2005.

(30) Foreign Application Priority Data

Mar. 17, 2005   (DK) .................................. 2005 00389

(51) Int. Cl.
*A61M 31/00* (2006.01)
(52) U.S. Cl. ..................................... 604/93.01
(58) Field of Classification Search ............... 604/93.01, 604/136, 116, 118
See application file for complete search history.

(56) References Cited

U.S. PATENT DOCUMENTS

| | | |
|---|---|---|
| 1,592,462 A | 7/1926 | MacGregor |
| 2,047,010 A | 7/1936 | Dickinson |
| 2,295,849 A | 9/1942 | Kayden |
| 2,690,529 A | 9/1954 | Lindblad |
| 2,936,141 A | 5/1960 | Rapata |
| 2,972,779 A | 2/1961 | Cowley |

(Continued)

FOREIGN PATENT DOCUMENTS

DE         4 342 329 A1    6/1994

(Continued)

OTHER PUBLICATIONS

International Preliminary Report on Patentability completed Apr. 2, 2007 for International Application No. PCT/DK2006/050005.

(Continued)

*Primary Examiner* — Kevin C Sirmons
*Assistant Examiner* — Deanna K Hall
(74) *Attorney, Agent, or Firm* — Brinks Hofer Gilson & Lione

(57) ABSTRACT

This invention relates to an injection site or gateway or a system comprising such an injection site or gateway. In one form the invention concerns a system comprising an inserter device and a gateway for subcutaneous injection of fluid where comprises a distal surface (1*a*) corresponding to a proximal surface (1*b*) integrated with the inserter device. In another form the invention concerns a gateway for subcutaneous injection of fluid, which gateway comprises —a body (1) with at least one through-going opening (6) with an entrance and an outlet, and at least one cannula (3) and having a proximal end protruding from the lower side of the body; —and at the entrance of the through-going opening medication can be injected by a delivery device (20) which delivery device has protruding parts (22) which form an inner opening with a diameter di; wherein the surface of the entrance is shaped in such a way that the cross-section of the top part of entrance, i.e. from the top of the entrance to a position di/3 below the top, do not exceed di.

19 Claims, 26 Drawing Sheets

U.S. PATENT DOCUMENTS

| | | |
|---|---|---|
| 3,059,802 A | 10/1962 | Mitchell |
| 3,074,541 A | 1/1963 | Roehr |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,545,286 A | 12/1970 | Stenstrom |
| 3,547,119 A | 12/1970 | Hall et al. |
| 3,610,240 A | 10/1971 | Harautuneian |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,525,157 A | 6/1985 | Vaillancourt |
| 4,530,695 A | 7/1985 | Phillips et al. |
| 4,531,937 A | 7/1985 | Yates |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,487,506 A | 1/1996 | Drummond et al. |
| 5,490,841 A | 2/1996 | Landis |
| 5,492,313 A | 2/1996 | Pan et al. |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,519,167 A | 5/1996 | Kunimoto et al. |
| 5,520,654 A | 5/1996 | Wahlberg |
| 5,522,803 A | 6/1996 | Teissen-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |

| | | | | | | |
|---|---|---|---|---|---|---|
| 5,586,553 A | 12/1996 | Halili | | 6,105,218 A | 8/2000 | Reekie |
| 5,591,188 A | 1/1997 | Waisman | | 6,106,498 A | 8/2000 | Friedli et al. |
| 5,599,309 A | 2/1997 | Marshall et al. | | 6,120,482 A | 9/2000 | Szabo |
| 5,599,315 A | 2/1997 | McPhee | | 6,123,690 A | 9/2000 | Mejslov |
| 5,599,318 A | 2/1997 | Sweeney et al. | | 6,132,755 A | 10/2000 | Eicher et al. |
| 5,628,765 A | 5/1997 | Morita | | 6,139,534 A | 10/2000 | Niedospial, Jr. |
| 5,643,214 A | 7/1997 | Marshall | | 6,159,181 A | 12/2000 | Crossman et al. |
| 5,643,216 A | 7/1997 | White | | 6,183,464 B1 | 2/2001 | Sharp et al. |
| 5,643,220 A | 7/1997 | Cosme | | 6,191,338 B1 | 2/2001 | Haller |
| 5,662,617 A | 9/1997 | Odell et al. | | 6,193,694 B1 | 2/2001 | Bell et al. |
| 5,665,071 A | 9/1997 | Wyrick | | 6,210,420 B1 | 4/2001 | Mauze et al. |
| 5,665,075 A | 9/1997 | Gyure et al. | | 6,219,574 B1 | 4/2001 | Cormier et al. |
| 5,676,156 A | 10/1997 | Yoon | | 6,221,058 B1 | 4/2001 | Kao et al. |
| 5,681,323 A | 10/1997 | Arick | | 6,248,093 B1 | 6/2001 | Moberg |
| 5,695,476 A | 12/1997 | Harris | | 6,293,925 B1 | 9/2001 | Safabash et al. |
| 5,697,907 A | 12/1997 | Gaba | | 6,302,866 B1 | 10/2001 | Marggi |
| 5,700,250 A | 12/1997 | Erskine | | 6,319,232 B1 | 11/2001 | Kashmer |
| 5,702,371 A | 12/1997 | Bierman | | 6,322,535 B1 | 11/2001 | Hitchins et al. |
| 5,704,920 A | 1/1998 | Gyure | | 6,322,808 B1 | 11/2001 | Trautman et al. |
| 5,709,516 A | 1/1998 | Peterson et al. | | 6,334,856 B1 | 1/2002 | Allen et al. |
| 5,714,225 A | 2/1998 | Hansen et al. | | 6,355,021 B1 | 3/2002 | Nielsen et al. |
| 5,738,641 A | 4/1998 | Watson et al. | | 6,379,335 B1 | 4/2002 | Rigon et al. |
| 5,741,288 A | 4/1998 | Rife | | D456,692 S | 5/2002 | Epstein |
| 5,752,923 A | 5/1998 | Terwilliger | | 6,387,076 B1 | 5/2002 | Landuyt |
| 5,807,316 A | 9/1998 | Teeple | | 6,387,078 B1 | 5/2002 | Gillespie, III |
| 5,810,835 A | 9/1998 | Ryan et al. | | 6,405,876 B1 | 6/2002 | Seshimoto et al. |
| 5,817,058 A | 10/1998 | Shaw | | 6,440,096 B1 | 8/2002 | Lastovich et al. |
| 5,820,598 A | 10/1998 | Gazza et al. | | 6,447,482 B1 | 9/2002 | Rønborg et al. |
| 5,827,236 A | 10/1998 | Takahashi | | 6,450,992 B1 | 9/2002 | Cassidy, Jr. |
| 5,833,666 A | 11/1998 | Davis et al. | | 6,488,663 B1 | 12/2002 | Steg |
| D402,538 S | 12/1998 | Wagter et al. | | 6,503,222 B2 | 1/2003 | Lo |
| 5,843,001 A | 12/1998 | Goldenberg | | 6,517,517 B1 | 2/2003 | Farrugia et al. |
| 5,848,990 A | 12/1998 | Cirelli et al. | | 6,520,938 B1 | 2/2003 | Funderburk et al. |
| 5,851,197 A | 12/1998 | Marano et al. | | D472,316 S | 3/2003 | Douglas et al. |
| 5,858,001 A | 1/1999 | Tsals et al. | | D472,630 S | 4/2003 | Douglas et al. |
| 5,865,806 A | 2/1999 | Howell | | 6,572,586 B1 | 6/2003 | Wojcik |
| 5,873,540 A | 2/1999 | Hardin | | 6,579,267 B2 | 6/2003 | Lynch et al. |
| 5,899,886 A | 5/1999 | Cosme | | 6,582,397 B2 | 6/2003 | Alesi et al. |
| 5,911,705 A | 6/1999 | Howell | | 6,595,962 B1 | 7/2003 | Perthu |
| 5,913,846 A | 6/1999 | Szabo | | 6,607,509 B2 | 8/2003 | Bobroff et al. |
| 5,915,640 A | 6/1999 | Wagter et al. | | 6,613,064 B2 | 9/2003 | Rutynowski et al. |
| 5,916,199 A | 6/1999 | Miles | | 6,620,133 B1 | 9/2003 | Steck |
| 5,919,167 A | 7/1999 | Mulhauser et al. | | 6,620,136 B1 | 9/2003 | Pressly, Sr. et al. |
| 5,925,032 A | 7/1999 | Clements | | 6,620,140 B1 | 9/2003 | Metzger |
| 5,947,931 A | 9/1999 | Bierman | | 6,629,949 B1 | 10/2003 | Douglas |
| 5,947,935 A | 9/1999 | Rinehart et al. | | 6,645,181 B1 | 11/2003 | Lavi et al. |
| 5,951,523 A | 9/1999 | Osterlind et al. | | 6,645,182 B1 | 11/2003 | Szabo |
| 5,954,643 A | 9/1999 | VanAntwerp et al. | | 6,659,982 B2 | 12/2003 | Douglas et al. |
| 5,957,892 A | 9/1999 | Thorne | | 6,685,674 B2 | 2/2004 | Douglas et al. |
| 5,968,011 A | 10/1999 | Larsen et al. | | 6,699,218 B2 | 3/2004 | Flaherty et al. |
| 5,975,120 A | 11/1999 | Novosel | | 6,702,779 B2 | 3/2004 | Connelly et al. |
| 5,980,488 A | 11/1999 | Thorne | | 6,726,649 B2 | 4/2004 | Swenson et al. |
| 5,980,506 A | 11/1999 | Mathiasen | | 6,736,797 B1 | 5/2004 | Larsen et al. |
| 5,984,224 A | 11/1999 | Yang | | 6,749,587 B2 | 6/2004 | Flaherty |
| 5,984,897 A | 11/1999 | Peterson et al. | | 6,749,589 B1 | 6/2004 | Douglas et al. |
| 5,992,787 A | 11/1999 | Burke | | 6,755,805 B1 | 6/2004 | Reid |
| D417,733 S | 12/1999 | Howell et al. | | 6,776,775 B1 | 8/2004 | Mohammad |
| 6,017,328 A | 1/2000 | Fischell et al. | | 6,790,199 B1 | 9/2004 | Gianakos |
| 6,017,598 A | 1/2000 | Kreischer et al. | | 6,805,686 B1 | 10/2004 | Fathallah et al. |
| D421,119 S | 2/2000 | Musgrave et al. | | 6,808,506 B2 | 10/2004 | Lastovich et al. |
| 6,024,727 A | 2/2000 | Thorne et al. | | 6,811,545 B2 | 11/2004 | Vaillancourt |
| 6,039,629 A | 3/2000 | Mitchell | | 6,814,720 B2 | 11/2004 | Olsen et al. |
| 6,042,570 A | 3/2000 | Bell et al. | | 6,824,530 B2 | 11/2004 | Wagner et al. |
| 6,045,533 A | 4/2000 | Kriesel et al. | | 6,824,531 B1 | 11/2004 | Zecha, Jr. et al. |
| 6,045,534 A | 4/2000 | Jacobsen et al. | | 6,830,562 B2 | 12/2004 | Mogensen et al. |
| 6,050,976 A | 4/2000 | Thorne et al. | | 6,837,877 B2 | 1/2005 | Zurcher |
| 6,053,893 A | 4/2000 | Bucher | | 6,837,878 B2 | 1/2005 | Smutney et al. |
| 6,053,930 A | 4/2000 | Ruppert | | 6,840,922 B2 | 1/2005 | Nielsen et al. |
| 6,056,718 A | 5/2000 | Funderburk et al. | | 6,880,701 B2 | 4/2005 | Bergeron et al. |
| 6,056,726 A | 5/2000 | Isaacson | | 6,916,017 B2 | 7/2005 | Noe |
| 6,074,369 A | 6/2000 | Sage et al. | | 6,923,791 B2 | 8/2005 | Douglas |
| 6,074,371 A | 6/2000 | Fischell | | 6,926,694 B2 | 8/2005 | Marano-Ford et al. |
| 6,077,244 A | 6/2000 | Botich et al. | | 6,939,331 B2 | 9/2005 | Ohshima |
| 6,086,008 A | 7/2000 | Gray et al. | | 6,949,084 B2 | 9/2005 | Marggi et al. |
| 6,086,575 A | 7/2000 | Mejslov | | 6,959,812 B2 | 11/2005 | Reif et al. |
| 6,090,068 A | 7/2000 | Chanut | | 6,960,193 B2 | 11/2005 | Rosenberg |
| 6,093,172 A | 7/2000 | Funderburk et al. | | 6,979,316 B1 | 12/2005 | Rubin et al. |
| 6,093,179 A | 7/2000 | O'Hara et al. | | 6,991,619 B2 | 1/2006 | Marano-Ford et al. |
| 6,099,503 A | 8/2000 | Stardella | | 6,991,620 B2 | 1/2006 | Marano-Ford et al. |

| Patent/Publication | Date | Inventor |
|---|---|---|
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,407,491 B2 | 8/2008 | Fangrow, Jr. |
| 7,407,493 B2 | 8/2008 | Cane+ |
| 7,431,876 B2 | 10/2008 | Mejlhede et al. |
| 7,569,262 B2 | 8/2009 | Szabo et al. |
| 7,648,494 B2 | 1/2010 | Kornerup et al. |
| 7,766,867 B2 | 8/2010 | Lynch et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0068904 A1 | 6/2002 | Pluth et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0145073 A1 | 10/2002 | Swanson |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183604 A1* | 12/2002 | Gowda et al. ................. 600/345 |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0009131 A1* | 1/2003 | Van Antwerp et al. ....... 604/111 |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0087913 A1 | 3/2004 | Rogers et al. |
| 2004/0068231 A1 | 4/2004 | Blondeau |
| 2004/0069044 A1 | 4/2004 | Lavi et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1* | 5/2005 | Fangrow, Jr. ............. 604/164.01 |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Konerup et al. |
| 2005/0240154 A1 | 10/2005 | Mogensen et al. |

| | | | |
|---|---|---|---|
| 2005/0251098 A1 | 11/2005 | Wyss et al. | |
| 2005/0256456 A1 | 11/2005 | Marano-Ford et al. | |
| 2005/0261629 A1 | 11/2005 | Marano-Ford et al. | |
| 2005/0277892 A1 | 12/2005 | Chen | |
| 2005/0283114 A1 | 12/2005 | Bresina et al. | |
| 2006/0015063 A1 | 1/2006 | Butikofer et al. | |
| 2006/0015076 A1 | 1/2006 | Heinzerling et al. | |
| 2006/0030815 A1 | 2/2006 | Csincsura et al. | |
| 2006/0036214 A1 | 2/2006 | Mogensen et al. | |
| 2006/0041224 A1 | 2/2006 | Jensen | |
| 2006/0069351 A9 | 3/2006 | Safabash et al. | |
| 2006/0069382 A1 | 3/2006 | Pedersen | |
| 2006/0069383 A1 | 3/2006 | Bogaerts et al. | |
| 2006/0095003 A1 | 5/2006 | Marano-Ford et al. | |
| 2006/0095014 A1 | 5/2006 | Ethelfeld | |
| 2006/0106346 A1 | 5/2006 | Sullivan et al. | |
| 2006/0129123 A1 | 6/2006 | Wojcik | |
| 2006/0135908 A1 | 6/2006 | Liniger et al. | |
| 2006/0135913 A1 | 6/2006 | Ethelfeld | |
| 2006/0142698 A1 | 6/2006 | Ethelfeld | |
| 2006/0161108 A1 | 7/2006 | Mogensen et al. | |
| 2006/0173410 A1 | 8/2006 | Moberg et al. | |
| 2006/0173413 A1 | 8/2006 | Fan | |
| 2006/0184104 A1 | 8/2006 | Cheney, II et al. | |
| 2006/0184140 A1 | 8/2006 | Okiyama | |
| 2006/0200073 A1 | 9/2006 | Radmer et al. | |
| 2006/0241551 A1 | 10/2006 | Lynch et al. | |
| 2006/0247553 A1 | 11/2006 | Diermann et al. | |
| 2006/0247574 A1 | 11/2006 | Maule et al. | |
| 2006/0253085 A1 | 11/2006 | Geismar et al. | |
| 2006/0253086 A1 | 11/2006 | Moberg et al. | |
| 2006/0264835 A1 | 11/2006 | Nielsen et al. | |
| 2006/0264890 A1 | 11/2006 | Moberg et al. | |
| 2007/0005017 A1 | 1/2007 | Alchas et al. | |
| 2007/0016129 A1 | 1/2007 | Liniger et al. | |
| 2007/0016159 A1 | 1/2007 | Sparholt et al. | |
| 2007/0021729 A1 | 1/2007 | Mogensen et al. | |
| 2007/0049865 A1 | 3/2007 | Radmer et al. | |
| 2007/0049870 A1 | 3/2007 | Gray et al. | |
| 2007/0066955 A1 | 3/2007 | Sparholt et al. | |
| 2007/0088271 A1 | 4/2007 | Richards et al. | |
| 2007/0093754 A1 | 4/2007 | Mogensen | |
| 2007/0104596 A1 | 5/2007 | Preuthun et al. | |
| 2007/0112301 A1 | 5/2007 | Preuthun et al. | |
| 2007/0112303 A1 | 5/2007 | Liniger | |
| 2007/0129688 A1 | 6/2007 | Scheurer et al. | |
| 2007/0173767 A1 | 7/2007 | Lynch et al. | |
| 2007/0191772 A1 | 8/2007 | Wojcik | |
| 2007/0191773 A1 | 8/2007 | Wojcik | |
| 2007/0203454 A1 | 8/2007 | Shermer et al. | |
| 2007/0185441 A1 | 9/2007 | Fangrow, Jr. | |
| 2007/0213673 A1 | 9/2007 | Douglas | |
| 2007/0179444 A1 | 10/2007 | Causey et al. | |
| 2007/0244448 A1 | 10/2007 | Lastovich et al. | |
| 2008/0312601 A1 | 12/2008 | Cane' | |
| 2010/0004597 A1 | 1/2010 | Gyrn et al. | |
| 2010/0137829 A1 | 6/2010 | Nielsen et al. | |
| 2010/0228226 A1 | 9/2010 | Nielsen | |

FOREIGN PATENT DOCUMENTS

| | | |
|---|---|---|
| DE | 196 31 921 A1 | 3/1997 |
| DE | 299 05 072 U1 | 9/1999 |
| DE | 101 17 285 A1 | 11/2002 |
| DE | 203 20 207 U1 | 11/2004 |
| DK | 1 360 970 | 11/2003 |
| DK | 1 475 113 A1 | 11/2004 |
| EP | 0 117 632 B1 | 9/1984 |
| EP | 0 239 244 B1 | 2/1987 |
| EP | 0272530 A2 | 6/1988 |
| EP | 0 451 040 A1 | 10/1991 |
| EP | 0 544 837 B1 | 6/1993 |
| EP | 0 651 662 B1 | 5/1995 |
| EP | 0652027 A1 | 5/1995 |
| EP | 0 657 184 A1 | 6/1995 |
| EP | 0 714 631 B1 | 6/1996 |
| EP | 0 744 183 A2 | 11/1996 |
| EP | 0 747 006 A1 | 12/1996 |
| EP | 0799626 A1 | 10/1997 |
| EP | 0 688 232 B1 | 12/1998 |
| EP | 0937475 A2 | 8/1999 |
| EP | 0 956 879 A1 | 11/1999 |
| EP | 0 615 768 A2 | 12/1999 |
| EP | 1 086 718 A1 | 3/2001 |
| EP | 1 125 593 A1 | 8/2001 |
| EP | 0 775 501 B1 | 6/2002 |
| EP | 1 329 233 A1 | 7/2003 |
| EP | 1380837 A1 | 10/2003 |
| EP | 1 380 315 A1 | 1/2004 |
| EP | 1 407 747 A1 | 4/2004 |
| EP | 1407793 A1 | 4/2004 |
| EP | 1 421 968 A2 | 5/2004 |
| EP | 1177802 B1 | 9/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1616594 A1 | 1/2006 |
| EP | 1704889 A1 | 9/2006 |
| EP | 1762259 A1 | 3/2007 |
| FR | 2725902 A1 | 10/1994 |
| GB | 478803 | 1/1938 |
| GB | 906574 | 9/1962 |
| GB | 2 088 215 A | 6/1982 |
| GB | 2 230 702 A | 10/1990 |
| JP | A-03-191965 A | 8/1991 |
| JP | 7051251 A | 11/1995 |
| JP | A-08-187286 A | 7/1996 |
| JP | A-10-179734 A | 7/1998 |
| JP | 2002-028246 A | 1/2002 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 96/20021 A1 | 7/1996 |
| WO | WO 96/32981 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/53220 A2 | 7/2002 |
| WO | WO 02/081012 A2 | 10/2002 |
| WO | WO 02/81012 A2 | 10/2002 |
| WO | WO 02/81013 A2 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/68014 A3 | 1/2003 |
| WO | WO 03/015860 A1 | 2/2003 |
| WO | WO 03/036728 A1 | 4/2003 |
| WO | WO 03/068305 A1 | 8/2003 |
| WO | WO 03/075980 A1 | 9/2003 |
| WO | WO 03/095003 A1 | 11/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |

| | | | |
|---|---|---|---|
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/082782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |

OTHER PUBLICATIONS

Unomedical A/S: "http://web.archive.org/web/20040906102448/http://www.infusion-set.com/Default.asp?I D=108" Internet Product Overview, Sep. 6, 2004, XP002408230.

"Why inset®?" inset® infusion set product overview; http://web.archive.org/web/20040906102448/http://www.infusion-set.com/Default.asp?ID=108; two pages.

* cited by examiner

GATEWAY SYSTEM

This application is a continuation of International Application No. PCT/DK2006/050005, filed Feb. 23, 2006, which claims the benefit of U.S. Provisional Application Ser. No. 60/662,667, filed Mar. 17, 2005 and Danish Patent Application No. PA 200500389, filed Mar. 17, 2005, these references are incorporated herein in their entirety.

BACKGROUND OF THE INVENTION

This invention relates to an injection site or gateway or a system comprising such an injection site or gateway. The gateway is placed subcutaneously in the user can replace repeated injections by syringes or injection pens which will reduce trauma to the patients' skin and at the same time keep the injection place free of infections.

Gateways as such are already known. In previous documents the use of a needle assembly comprising a gateway and a pen-type injector is disclosed by this assembly it is possible to provide subcutaneous or intravenous injections using a blunt tipped needle. It is not indicated in the documents how the gateway is inserted. It would not be possible to use even a relatively short, sharp needle for injection in this gateway as the risk of penetrating the side of the soft cannula with a hypodermic needle would be considerable, as the steering or piloting of the needle when penetrating the septum is small and at the same time the hard case housing is very short.

Also other types of gateways are known, e.g. gateways comprising an elongated housing having an internal passageway extending from one end of the housing to the opposite end in the longitudinal sense. A cannula tube is connected to the housing and extends from the distal end of the passageway. The cannula tube is connected to the housing by means of a bushing and immediately adjacent to the proximal end of the cannula is a self-sealing silicon membrane. The membrane is in the form of a plug engaging the rear end of the bushing. In this way there is only a minimum of dead space i.e. internal volume in the passageway of the housing. This gateway has a rather long hard case housing which reduces the risk of penetrating the cannula with a sharp needle, but the gateway is also intended to be inserted manually in a very low angle. After insertion the gateway is placed almost parallel to the patients' skin and this parallel position can make it difficult for the patients themselves to inject medical substances through the gateway.

It is an aim of the present invention to provide a gateway which is easy for the patient to place and to use for self-administration of drugs or other medicaments. Also it is an aim that the gateway after placement onto the patients' skin is noticed as little as possible by the patient when the patient is not actually injecting medication.

SUMMARY OF THE INVENTION

According to the present invention an injection prepared gateway for subcutaneous injection of fluid, which gateway comprises: a body with a through-going opening; a mounting pad attached unreleasably to the body and having an adhesive surface; at least one cannula and at least one penetrating member having a proximal end protruding from the lower side of the body; a septum placed at the distal end of the cannula in the through-going opening; where the septum restricts the access to the cannula, so access to the cannula can be reached by a drug delivery device being able to penetrate the septum. The gateway is releasably connected to a biasing unit in an inserter part which part can bring the gateway from a retracted to a forward position when released.

Preparing the gateway for injection by placing it in an injector assures that a non-skilled user can perform a correct subcutaneously placement of the gateway under sterile conditions. A correct placement of the gateway is essential for a completely user controlled operation of medication. Preferably the injector is of a single use type as for example known from WO 03/026728 (Inset™). After injection the gateway is secured to the patient by the mounting pad and due to a smooth surface and low height of the body of the gateway it is unlikely that the gateway get caught in anything. That the gateway has a smooth surface means that the surface all the way around the body especially at the edge close to the mounting pad is without protrusions, openings and pointing corners. The desire to keep the surface smooth can generally cause a problem when the unit has to be fastened firmly inside an inserter during insertion but this problem has been solved according to the present invention.

The word "cannula" is used for a hollow member protruding from the body of the gateway; the cannula is inserted into the patient and leads the fluid drug from the inside of the gateway and into the body of the patient. A cannula can function as penetrating member if it is made of a hard material such as metal or a hard plastic, and in this case the cannula and the penetrating member are one and the same. Preferably the cannula of the injection prepared gateway is made of a soft material as the soft cannula is more compatible with the skin tissue than a hard cannula. In this case it will be necessary to have a separate penetrating member such as a pointy needle which can cut an opening in the patients' skin and prepare the entering of the cannula, after insertion of the soft cannula the penetrating member will be removed while leaving the cannula in the patients skin as a pass way for the drugs to be delivered. Also it is preferred that the penetrating member in the form of an insertion needle is fastened unreleasably to the inserter device and extending inside and beyond the cannula, in this situation the insertion needle will be removed together with the inserter device and the user will not have to remove a separate needle or needle unit after having removed the inserter device.

In one embodiment of the invention more than one cannula and/or penetrating members are protruding from the lower side of the body of the gateway.

This could be the case if the single penetrating member was replaced with a group of shorter penetrating members only protruding a few millimeters and being supplied with medication from a common chamber inside the body of the gateway.

It could also be the case if the gateway was to be used together with a metering unit for e.g. glucoses in the blood. When used as a continuous metering device with the possibility of simultaneous administration of medication, the patient will need to have a probe inserted which could provide the metering device with access to the blood. The probe can be inserted together with the cannula through which the medication is injected or it can be inserted at another position by another penetrating member. In a preferred embodiment the gateway can perform as a base for a metering device such as the device Navigator™ sold by Abbotts Diabetes Care.

Preferably the injection prepared gateway is provided with a steering part which will make it easier for a user to perform injections through the gateway once the gateway has been inserted. This will be a significant advantage for patients with bad eyesight or in situations where the gateway is placed at positions on the patients' body where it is difficult for the patient to see the entrance of the injection needle.

According to the present invention the steering part can both be placed inside the through-going opening and on the distal surface of the body of the gateway.

If the steering part is placed on the distal surface, the steering part can have the form of tracks, which tracks can be both protruding and/or recessing from the surface. Preferably the tracks form an opposite impression of a part of the inserter device, preferably formed as the injection end of an injection pen.

In a preferred embodiment the tracks are formed as one or more recesses, preferably of a circular form which will allow for the injection pen to have prolonged sides covering the needle when the injection pen is not used for injection, and protecting the user against needle sticks.

In a preferred embodiment the releasable part of the steering part forms a unique interface between the drug delivery device and the gateway and assures that it is only possible to use one given injector device. "Unique interface" means that the two surfaces facing each other i.e. the surface of the gateway and the surface of the drug delivery device correspond to each other like hand and glove. This is an advantage if for example a given injector device is used for a certain drug which will make it almost impossible for the patient to inject a drug not prescribed to the patient. Also an interface which causes a very close fit between the drug delivery device and the gateway will ensure a minimum of dead space, that is internal volume inside the body of the gateway where an injected medicament stay unused. In another preferred embodiment at least a part of the steering part is releasably fastened to the body in order for the releasable part to act as an interchangeable adaptor between a drug delivery device and the gateway.

The injection prepared gateway can be fastened releasably to a slidable member inside the inserter part which slidable member is unreleasably fastened to the biasing unit.

The reason why it is preferred to fasten the injection prepared gateway to a slidable member which is not identical with the biasing unit is that it is simpler to connect the gateway to a unit which has the purpose of forming a connection between the biasing unit and the gateway than it is to connect the gateway directly to the biasing unit, as the biasing unit has a well defined purpose already which makes demands to the design of the biasing unit. The slidable member can be of a very simple construction as it is possible to adequately fastened the gateway to the slidably member simply by attaching the insertion needle unreleasably to the slidable member and inserting the insertion needle into the cannula of the gateway. The frictional resistance alone between the insertion needle and the cannula will then keep the gateway in the right position during insertion.

Preferable the proximal side of inserter part which is in contact with the body of the gateway is shaped to correspond closely to the gateway. That the inserter part is shaped to correspond to the gateway means that the end of the inserter part which is adjacent to the gateway closely follows the surface of the gateway and creates the largest possible contact between the slidable member and the gateway. This large contact assures that the gateway is steered more precisely through the inserter which results in a very precise—and therefore more painless—insertion.

Preferably the end of the inserter part which is adjacent to the gateway is shaped as the end of an injection pen and the surface of the gateway is formed with corresponding tracks. A lot of gateway users prefer to insert medication with injection pens as this is an easy way to perform insertion and assure correct dosage. Forming the surface of the slidable member adjacent to the gateway as an injection pen will have the result that formed tracks in the surface of the gateway will suit equally well to the slidable member and an injection pen.

In order to protect the injection prepared gateway when it is attached to the user, a cover corresponding to the gateway can be positioned on top of the body between the insertions performed by the user.

The injection prepared gateway is especially directed towards the use of insulin and by using the injection prepared gateway it is possible e.g. to replace the use of an insulin pump. An insulin pump provides the patient with a steady dosage of insulin through a soft tube connected to an infusion part fastened to the patient but the pump is an expensive unit and it is inconvenient for the patient to—at least periodically—carry the device and connecting tubing on the body.

The invention also concerns a system comprising an inserter device and a gateway for subcutaneous injection of fluid where the gateway comprises a body with at least one through-going opening, at least one cannula and a restriction for microorganisms placed at the distal end of the at least one cannula or in the at least one through-going opening; and which system comprises at least one penetrating member having a proximal end protruding from the lower side of the body; drugs to be injected is delivered to the gateway by a drug delivery device being able to pass the restriction for microorganisms, the gateway is releasably connected to a biasing unit in the inserter device which unit can bring the gateway from a retracted to a forward position when released, wherein the body of the gateway comprises a distal surface corresponding to a proximal surface integrated with the inserter device.

The word "integrated" means that the proximal surface can constitute a surface of the inside of the inserter or that the proximal surface can be constituted of a part releasably or unreleasably fastened to the inside of the inserter. In a preferred embodiment the proximal surface integrated with the delivery device belongs to a separate interface. In this application the words "interface" and "adaptor" is used interchangeably.

The invention also concerns a system comprising an inserter device, a gateway and an interface, where the gateway comprises a body with at least one through-going opening, at least one cannula and a restriction for microorganisms placed at the distal end of the at least one cannula or in the at least one through-going opening; and which system comprises at least one penetrating member having a proximal end protruding from the lower side of the body; drugs to be injected is delivered to the gateway by a drug delivery device being able to pass the restriction for microorganisms, the gateway is releasably connected to a biasing unit in the inserter device which unit can bring the gateway from a retracted to a forward position when released, wherein the interface provides a distal surface corresponding to the inserter and a proximal surface corresponding to the gateway.

The invention also concerns a system comprising a drug delivery device and a gateway for subcutaneous injection of fluid where the gateway comprises a body with at least one through-going opening, at least one cannula and a restriction for microorganisms placed at the distal end of the at least one cannula or in the at least one through-going opening; and which system comprises at least one penetrating member having a proximal end protruding from the lower side of the body; drugs to be injected is delivered to the gateway by the drug delivery device being able to pass the restriction for microorganisms, the gateway is releasably connected to a biasing unit in an inserter device which unit can bring the gateway from a retracted to a forward position when released, wherein the system also comprises a separate interface comprising a proximal surface corresponding to a distal surface of the gateway and a distal surface corresponding to a proximal surface of the delivery device.

The invention also concerns a system comprising an inserter device, a drug delivery device and a gateway for subcutaneous injection of fluid where the gateway comprises a body with at least one through-going opening, at least one cannula and a restriction for microorganisms placed at the distal end of the at least one cannula or in the at least one through-going opening; and which system comprises at least one penetrating member having a proximal end protruding from the lower side of the body; drugs to be injected is delivered to the gateway by the drug delivery device being able to pass the restriction for microorganisms, the gateway is releasably connected to a biasing unit in the inserter device, which unit can bring the gateway from a retracted to a forward position when released, wherein the gateway comprises a distal surface corresponding to a proximal surface integrated with the inserter device and to a proximal surface integrated with the delivery device. Preferably the gateway comprises a distal surface corresponding to a proximal surface of an interface and the interface has a distal surface corresponding to a proximal surface of the delivery device.

The advantage of these systems are that when using the whole system it is possible to combine standard units which are relatively non-expensive to produce with e.g. drug specific units which are more expensive but can assure that no mistakes are made e.g. when a user has to administer more than one medication to him/her self. Further self-administration of medication encourages individuals to participate in their own health care and provides structure for regular assessment and teaching about their drugs.

In a preferred embodiment the distal surface of the gateway comprises a steering part constituted of one or more parts inserted in the opening which part or parts are made of a relatively hard material for example metal or hard plastic or the same material as the body is made of.

In a preferred embodiment at least a part of the steering part can be separated from the body and preferably the steering part is formed in a separate socket which is being fastened to the body of the gateway before use. Also in a preferred embodiment the interface comprises an injection needle.

In a preferred embodiment the part of the steering part which can be separated from the body functions as an adapter for a given drug delivery device.

According to the invention a separate interface can be secured to the delivery device. Preferably the separate interface can be moved from one position where it covers the injection needle to a second position where the injection needle is not covered.

The present invention also concerns a system comprising a drug delivery device with an insertion needle secured to an interface wherein an end of the interface which is not secured to the drug delivery device is provided with at least one cover in order to provide a protected and sterile environment around the insertion needle. Preferably the drug delivery device is filled with a drug in a ready-to-use condition.

The present invention also concerns a gateway for subcutaneous injection of fluid, which gateway comprises a body with at least one through-going opening with an entrance and an outlet, and at least one cannula placed in fluid connection with the through-going opening and having a proximal end protruding from the lower side of the body;

and at the entrance of the through-going opening medication can be injected by a delivery device which delivery device has protruding parts covering the entrance when delivering medication to the gateway and which protruding parts form an inner opening with a diameter $d_i$;

wherein the surface of the entrance is shaped in such a way that the cross-section of the top part of entrance, i.e. from the top of the entrance to a position $d_i/3$ below the top, do not exceed $d_i$. Preferably the surface of the top part is constructed as a part of a sphere. Alternatively the surface of the top part is constructed of several smaller plane surfaces connected to each other in angles above 90° forming a coherent, convex surface (multifaceted).

In a preferred embodiment the gateway has at least two through-going openings. Preferably at least one of the through-going openings has a wall which can not be penetrated by a pointy insertion needle placed opposite the entrance for the insertion needle.

Preferably the septum can be either pushed away from the entrance of a through-going opening or penetrated in order to enter a through-going opening.

Embodiments of the invention will now be described with reference to the figures in which.

Figure 1:
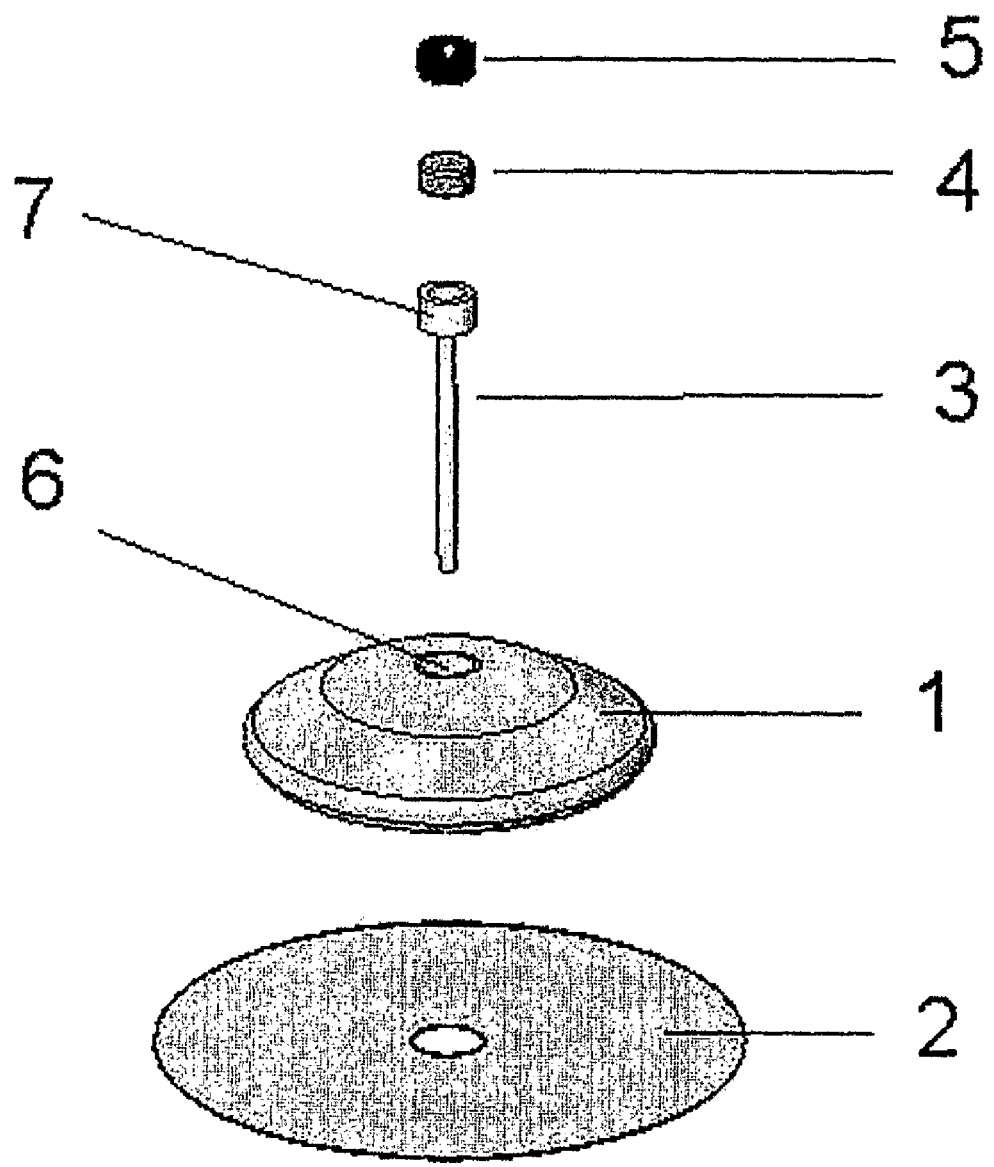
FIG. 1 is an exploded view of a gateway.

In FIG. 1 is shown an exploded view of a gateway. The gateway comprises a body 1 with a smooth distal surface, where the distal surface is the surface turned away from the patient after the gateway has been inserted, and at the proximal side of the body 1 is placed a mounting pad 2 having an adhesive surface proximal to the patient. The proximal side is the side turned towards the patient after the gateway has been inserted. The body 1 has a through-going opening 6 in which is placed a cannula 3 extending from the proximal side of the body 1. At the distal end of the cannula the diameter is increased which results in the forming of a small chamber 7 at this end of the cannula, this chamber functions as a deposit for fluid injected through the septum. In the through-going opening 6 is also placed a septum 4 which limits access to the opening 6 as the opening created in the septum 4 by a needle will be closed after removal of the needle due to the characteristics for the material chosen for the septum 4. It is necessary to use a relatively hard needle to penetrate the septum, but the needle does not need to be pointy. Relatively hard means that the needle has to be harder when compared to the material of the septum 4, the needle does not need to be made of steel; it could be made of e.g. hard plastic. In EP 1191964 it is described how to produce such a needle. At the distal end of the through-going opening 6, i.e. the end where the injection needle enters the opening 6 is placed a steering part 5; the steering part 5 is made of a relatively hard material and makes it easier to enter the needle into a correct position in the through-going opening 6. That the steering part is made of a relatively hard material means that it should not be possible to penetrate the steering part 5 by the injection needle, how hard the material needs to be then depends on which injection needle is used. Materials which could withstand penetration from commonly used pointy injection needles would be a hard plastic or a metal but if the injection needle is blunt it would be possible to use softer materials like rubber.

Figure 2:
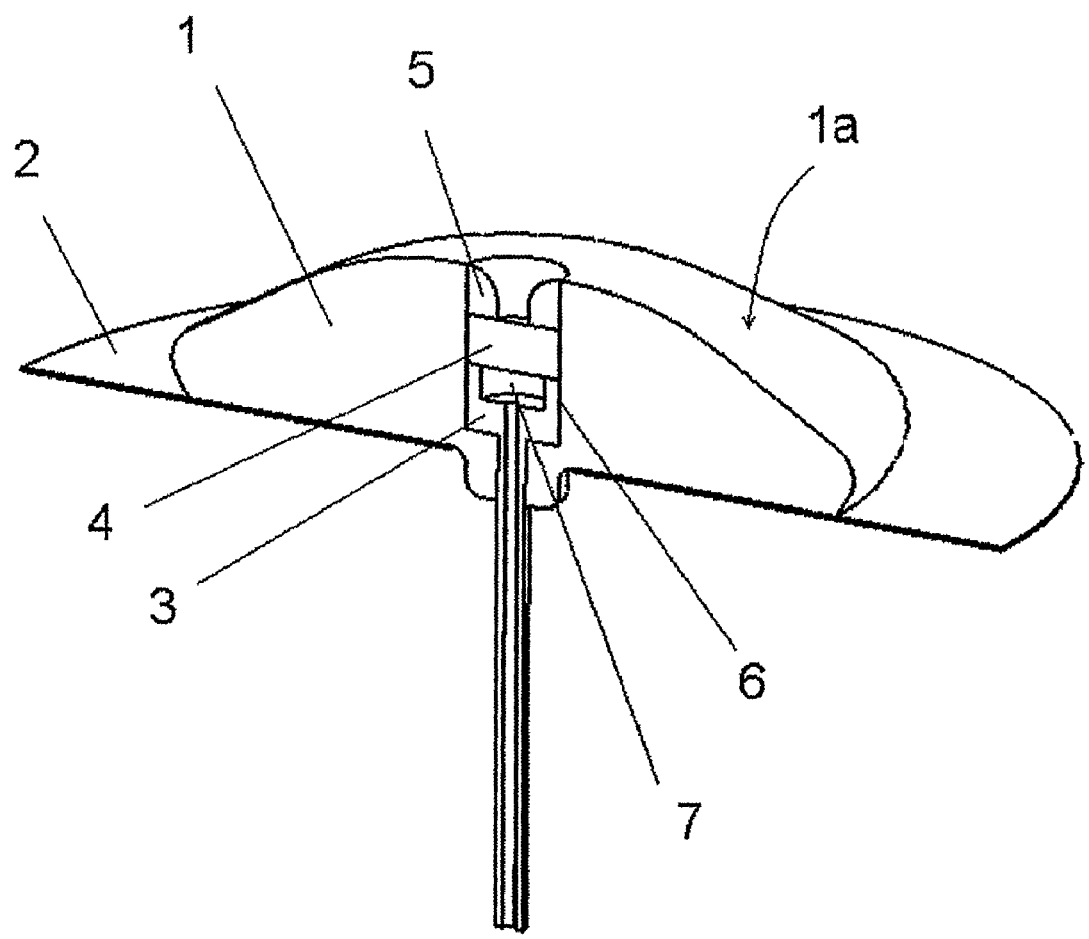
FIG. 2 is a cut-through drawing of the same embodiment as in FIG. 1.

FIG. 2 shows a cut through the same embodiment of a gateway as shown in FIG. 1. In this figure the mounting pad 2 is placed adjacent to the body 1. The cannula 3 is placed at the proximal end of the opening 6; adjacent to the cannula above the chamber 7 the septum 4 is placed. The steering part 5 is placed between the septum and the outer distal surface of the body 1. In this figure it is possible to see how the steering part 5 directs the needle into the correct position on the opposite side of the septum 4 and assures the injected fluid is placed in the chamber 7.

Figure 3A:
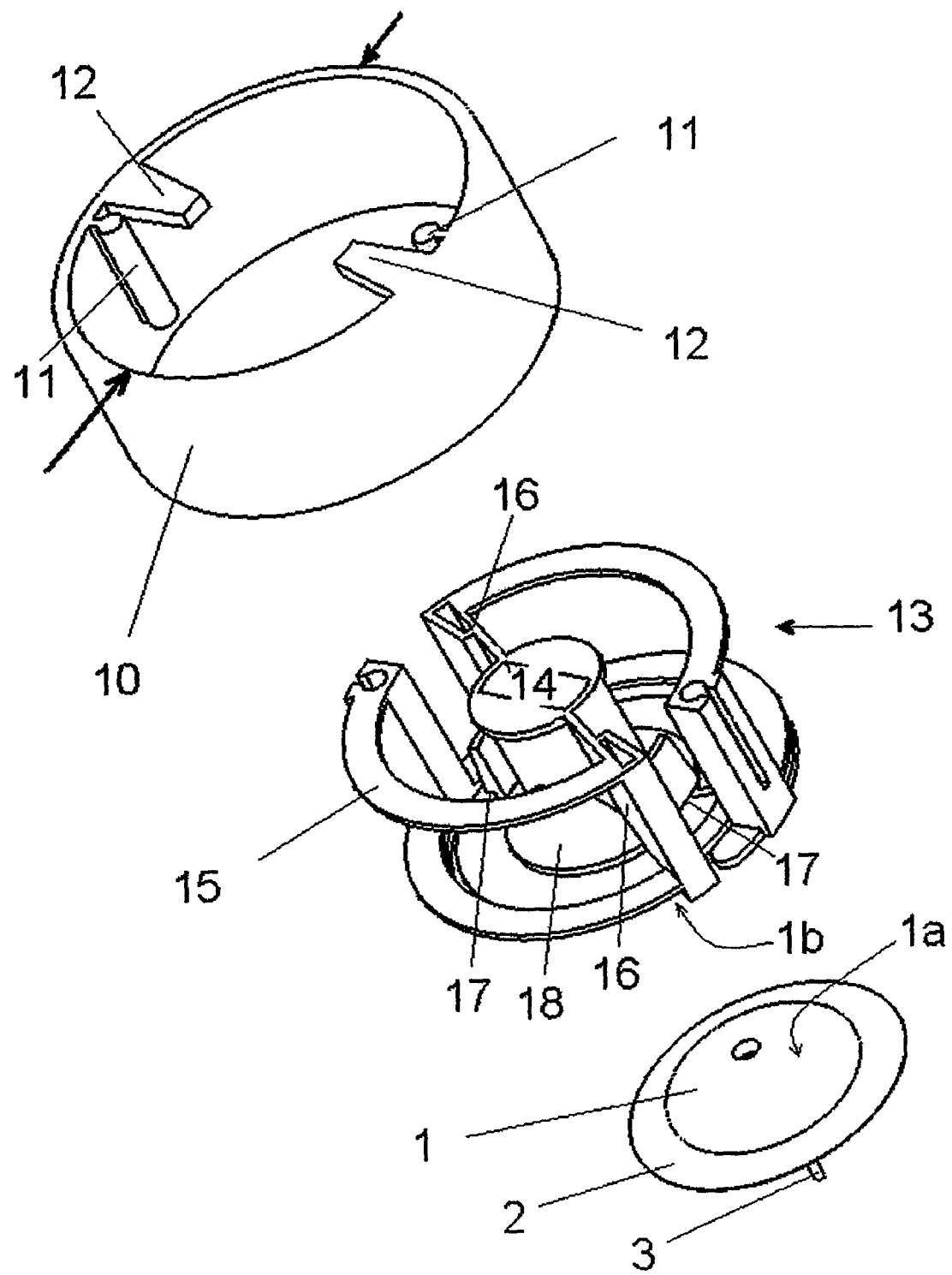
FIGS. 3A and 3B show an embodiment of an inserter for the gateway of FIGS. 1 and 2 in an exploded view.
Figure 3B:
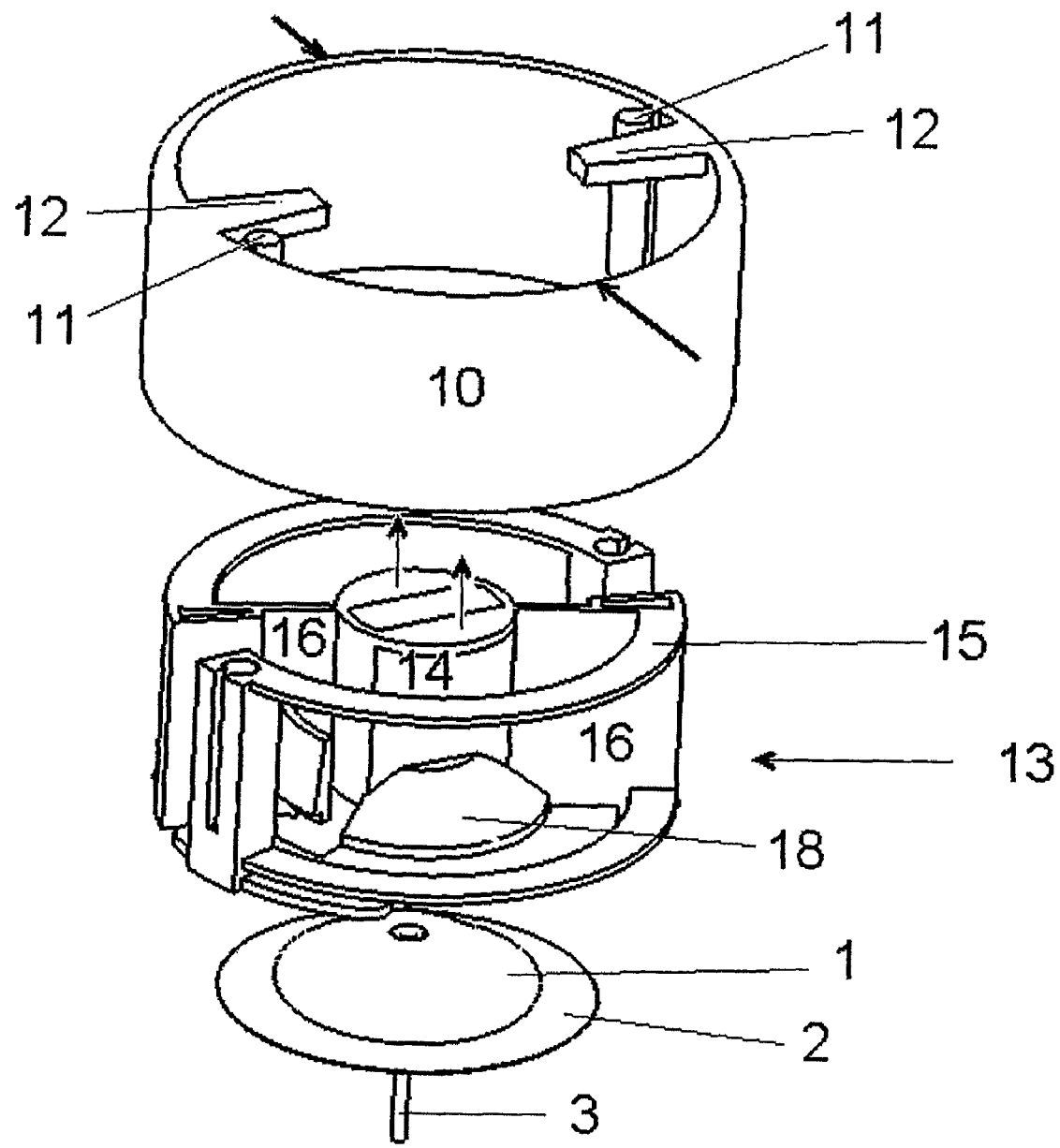

FIGS. 3A and 3B show an inserter device which can be used in accordance with the invention. The inserter comprises a housing 10, in this embodiment the housing 10 comprises two fastening elements 11 which assures that the insides 13 cannot rotate in relation to the housing. The housing also comprises detaining elements 12 in the form of two protruding parts keeping the insides 13 in a biased position until the insides 13 are released from the biased position by affecting some release means. The insides 13 are constructed of a central part 14 and a surrounding part 15. The central part 14 functions as a finger grip and the surrounding part 15 functions as a biasing unit. The central part 14 can slide between a forward and a retracted position in relation the housing 10 and the body 1 of the gateway is fastened to the central part 14.

The surrounding part 15 is constructed as two parts formed almost as semicircles, where one end of each semicircle is attached to one of the fastening elements 11 in the housing 10, and the other end of each semicircle is—via a connecting wall 16—fastened to the central part 14. The end of the semicircle fastened to the housing 10 at the fastening elements 11 does not move relatively to the housing 10 during use. The other end of the semicircle which is attached to the central part 14 with the finger grips will move relatively to the housing 10 when the central part 14 is pulled out of the housing 10 (arrows for direction in FIG. 3B). When pulling in the central part 14, the surrounding part 15 which functions as a biasing unit, will be tightened. The surrounding part 15 is kept in the biased position by two protrusions 17. The protrusions 17 are in this embodiment attached to the connecting wall 16 but could just as well be attached to the central part 14. When the central part 14 is pulled out of the housing 10, the protrusions 17 will be pulled past the detaining elements 12 and these elements will prevent the protrusion 17—and therefore also the central part 14—from returning to the relaxed position inside the housing 10.

As the housing 10 possesses certain flexibility the biasing position can be released by pressing on the sides of the housing at a line perpendicular to the line formed by the two detaining elements 12 (direction indicated by arrows on FIGS. 3A and 3B). When pressing at the two opposite sides in this position, the resulting deformation of the housing will cause the two detaining elements 12 to be pushed away from each other, thereby leaving enough room for the protrusions 17 to pass by the detaining elements 12 and for the central part 14 to be forced back into the relaxed position by the biasing unit 15.

The body 1 of the gateway is positioned at the proximal end of the central part 14. In the embodiment shown in FIGS. 3A and 3B the means 18 for engaging of the body 1 of the gateway has the form of a cupola. The body 1 of the gateway is placed with its distal side fitted into the cupola 18. The proximal side of the body 1 is covered with a mounting pad 2 and at least one insertion needle which is either attached to the central part 14 or to the body of the gateway protrudes from the proximal side through the mounting pad 2 when the body 1 is fastened to the inserter device 10, 13. If the insertion needle is attached to the inserter device 10, 13 the body 1 is provided with a cannula 3, preferably of a soft material.

When the injection prepared gateway is acquired by the user, the gateway will be placed in the inserter device and the whole unit will be sterilized. When the unit is sterilized it is necessary to provide the housing 10 with a removable cover on both the distal and the proximal end. The biasing unit 15 is in a relaxed state which means that the insides 13 is completely covered by the housing 10 while the insertion needle protrudes from the proximal side and requires a suitable cover which do not allow penetration by the sterile needle, preferably a relatively hard cover.

When the user is going to insert the gateway, the user first remove the two covers at the distal and the proximal end of the housing 10 and then the user removes the release liner of the mounting pad 2, if the mounting pad 2 is covered by a release liner. Afterwards the user grab the finger grip of the central part 14 and pull the central part 14 out of the housing in direction along the axis of the central part 14. The user pull until the protrusions 17 pass over the detaining elements 12 and a click is heard. The user then let go of the finger grip and leave the central part 14 in the tightened position. Now the injection prepared gateway is placed on the skin of the patient and the biasing unit 15 is released by squeezing lightly on the sides of the housing 10. It is marked by colorization or patterns where exactly on the housing 10 the user needs to squeeze in order to release the biasing unit.

When the biasing unit is released, the central part 14 moves back into the relaxed position inside the housing and because the insertion needle protrudes from the housing in the relaxed position, the insertion needle penetrates the patients' skin. When the insertion needle has penetrated the patients' skin, the inserter device 10, 13 is separated from the body 1 of the gateway and removed. The insertion needle will be removed together with the inserter device 10, 13 if the insertion needle is attached to the central part 14 but if the insertion needle is attached to the body of the gateway, the insertion needle will stay inserted and function as the cannula.

Other inserter devices than described here can be used together with the gateway according to the invention but it is necessary that it is possible to adapt the body of the gateway into the inserter devices and to keep it in position by preventing rotational movements until insertion has taken place. This can be difficult as the gateway preferably has a very smooth distal surface. This is contrary to the inserters for infusion sets as infusion sets comprises two parts: an infusion part which comprises a cannula being inserted in the patient's skin and a connector part. Because at least a part of the distal surface of the infusion part of an infusion set is provided with means for fastening the infusion part to the connector, the infusion part will always be provided with means for fastening the device inside an inserter.

In the above described inserter device 10, 13 the body 1 of the gateway is retained in the inserter device 10, 13 by the frictional resistance between the insertion needle and the cannula but there are other ways of retaining the body 1 of the gateway in the inserter device during insertion for example by applying an adhesive between the inserter device 10, 13 and the gateway, or by pressing the gateway into a restricted room formed by parts of the inserter device 10, 13. In order to assure it to be possible to disengage the gateway from the inserter device 10, 13 without the user having to somehow pull the gateway away from the inserter, the adherence between the inserter device 10, 13 and the gateway has to be smaller than the adherence between the mounting pad of the inserted gateway and the skin of the patient.

The present invention is directed especially to the use of both relatively short pointy needles as for example needles traditionally used in injections pens or blunt needles. For these two types of needles the steering part 5 assures a perfect entrance into the through-going opening 6 even for users without experience. The steering part 5 can be a very small unit placed inside the opening 6 and being flush with the distal surface of the body 1. In this case the distal surface of the body 1 can be made totally smooth without any protrusions or recesses which would be an advantage as it is very important that the body 1 do not unintentionally stick to or get caught of anything as the patient moves around. Alternatively the steering part 5 can be formed externally on the body 1 in the form of tracks corresponding to the needle unit used for injection. This form of the steering part 5 has the advantage of giving very easy and secure injections as the external steering part 5 assures there will be only on way to put the injection needle when injecting medication to the patient through the gateway.

If a blunt needle is used for injection of medication the septum 4 will most likely has to have a preshaped hole in order for the blunt needle to be able to pass through, although it will depend on the material used to make the septum 4. If the insertion needle is fastened unreleasably to the inserter device 10, 13 a preshaped hole will be formed in the septum 4 when the inserter device 10, 13 and the insertion needle attached hereto is removed after insertion.

Figure 4:
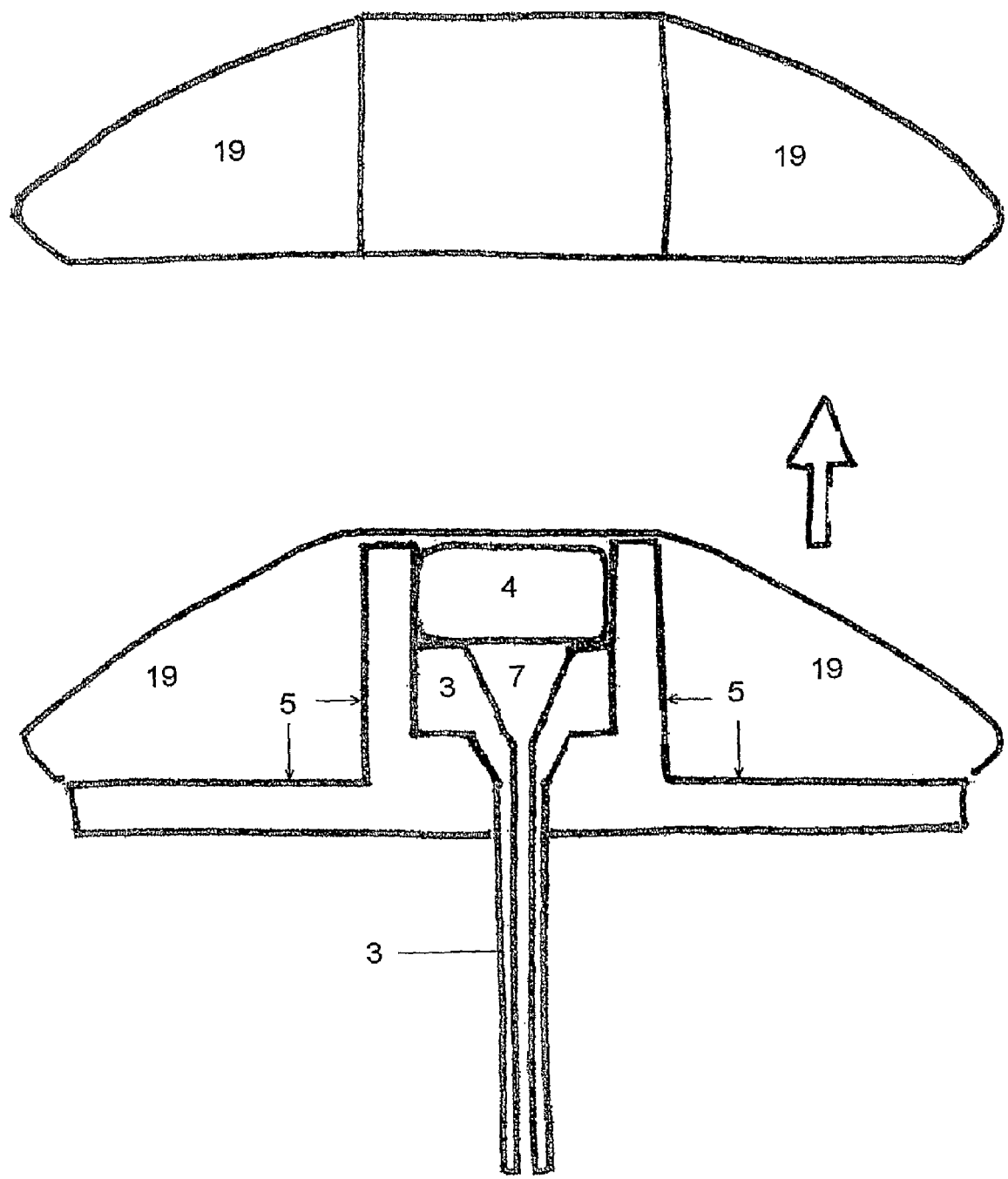
FIG. 4 shows a second embodiment of a gateway according to the invention where the gateway is provided a cover.

FIG. 4 shows a cut through a gateway. In this embodiment the steering part 5 is formed as a central part of the body 1 is constituted of several upright parts or one coherent preferably circular part extending from the plan approximately parallel to the patients skin. In order for the gateway not to catch on to anything when attached to the patient, the gateway is provided with a cover 19. The cover provides the body 1 of the gateway with a smooth surface, and the cover 19 can also function as an adapter or interface, if the patient wants to use different types of needle units, if the cover 19 is formed as a ring which do not completely cover the through-going opening 6 of the body or is provided with a penetrable material above at least a part of the opening 6.

Figure 5:
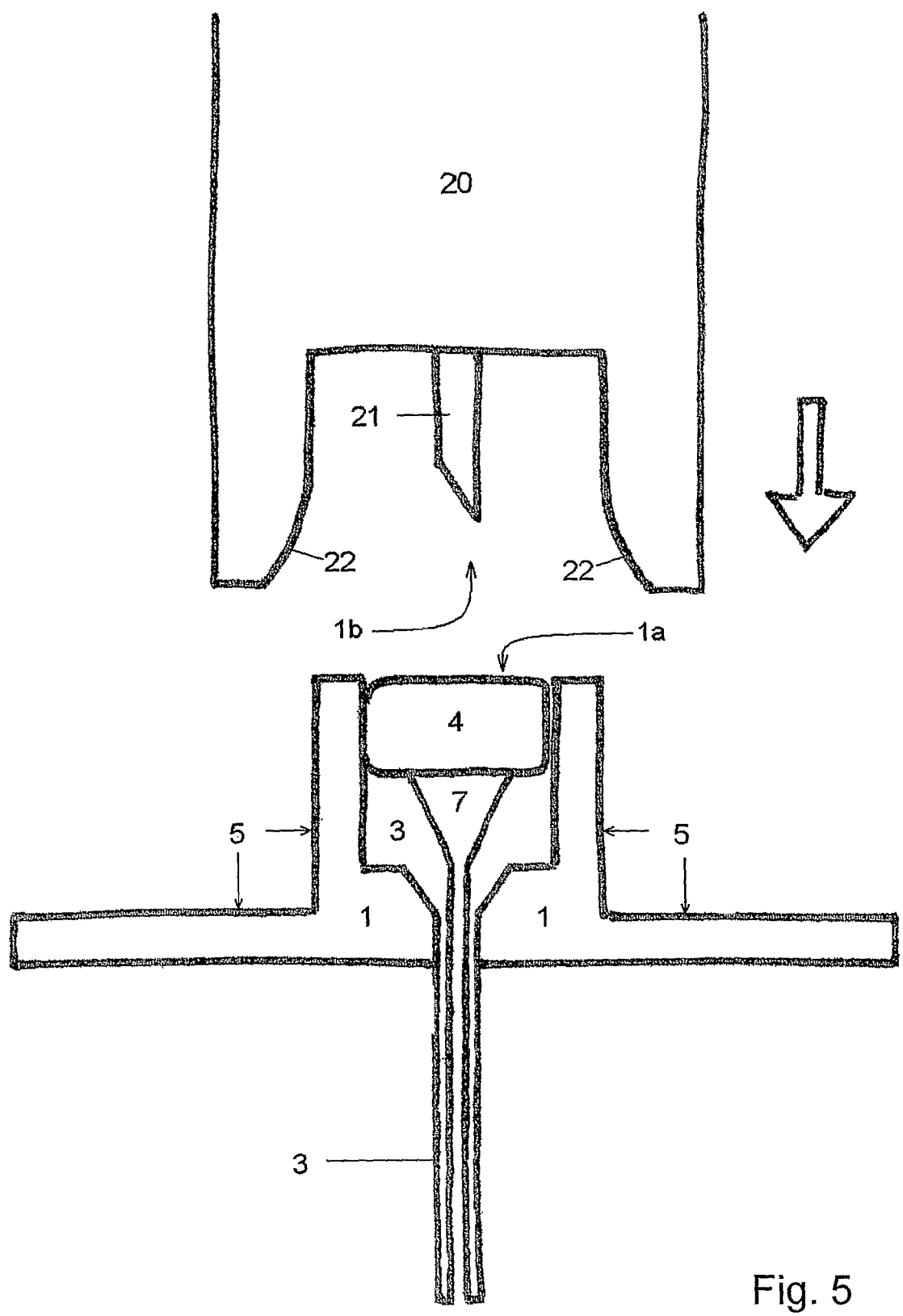
FIG. 5 shows the second embodiment of the gateway together with an injection needle.

FIG. 5 shows the same gateway as in FIG. 4 but now the cover 19 is removed from the gateway and the gateway is ready for injection of medication. The medication is injected with a syringe 20 provided with a pointy injection needle 21. In this embodiment the injection needle is retracted compared to the front part of the syringe. The front part of the syringe comprises one or more projecting parts 22, these parts are protecting the surroundings from the pointy needle before and after injection and are also corresponding to the steering part 5. The correspondence between the steering part 5 and the projecting parts 22 assures easy and secure injection because it is only possible to place the injection needle in the correct position when the steering part 5 and the projecting parts 22 have to fit together.

Figure 6A:
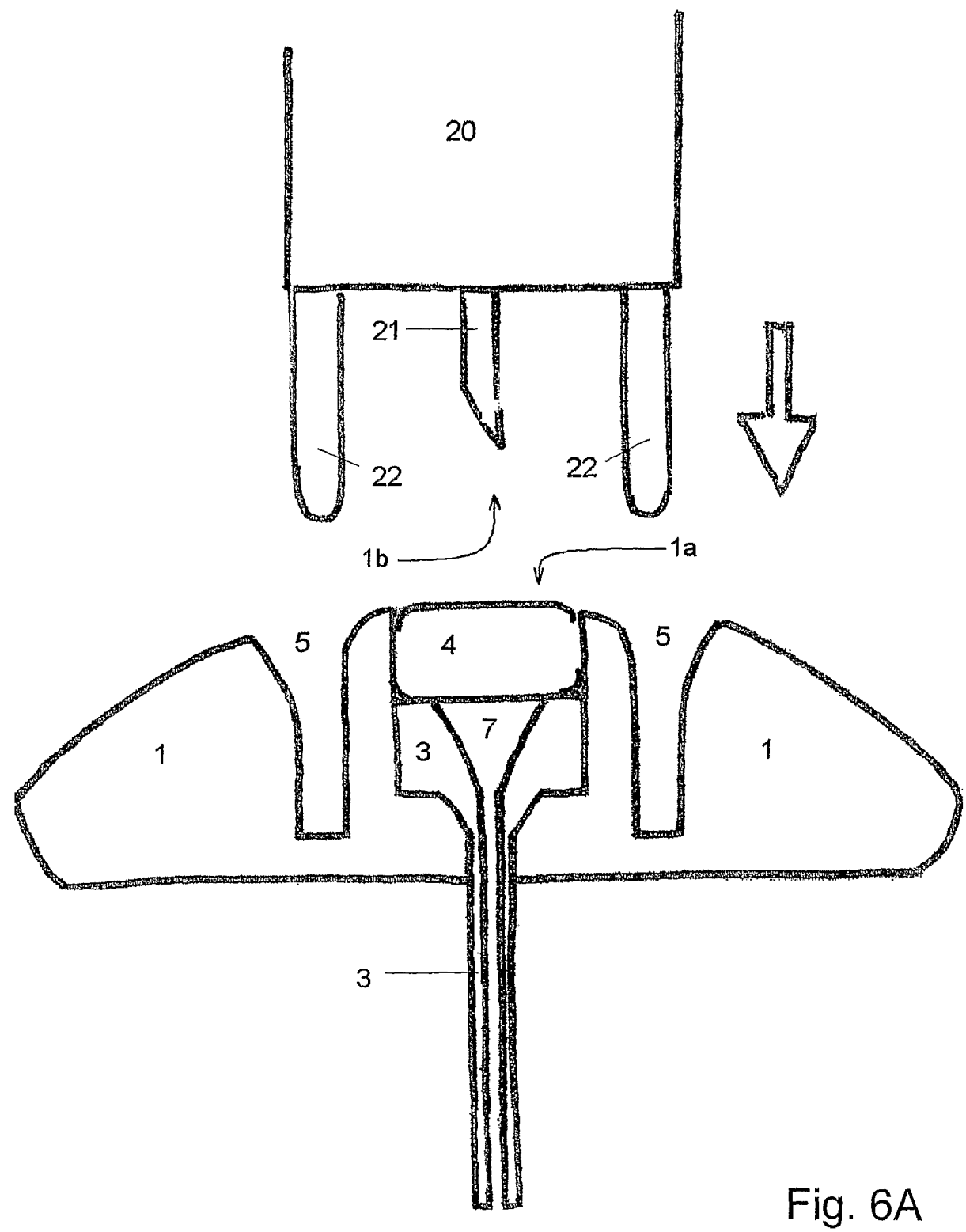
FIG. 6A shows a third embodiment of the gateway together with deep tracks and a corresponding injection needle.
Figure 6B:
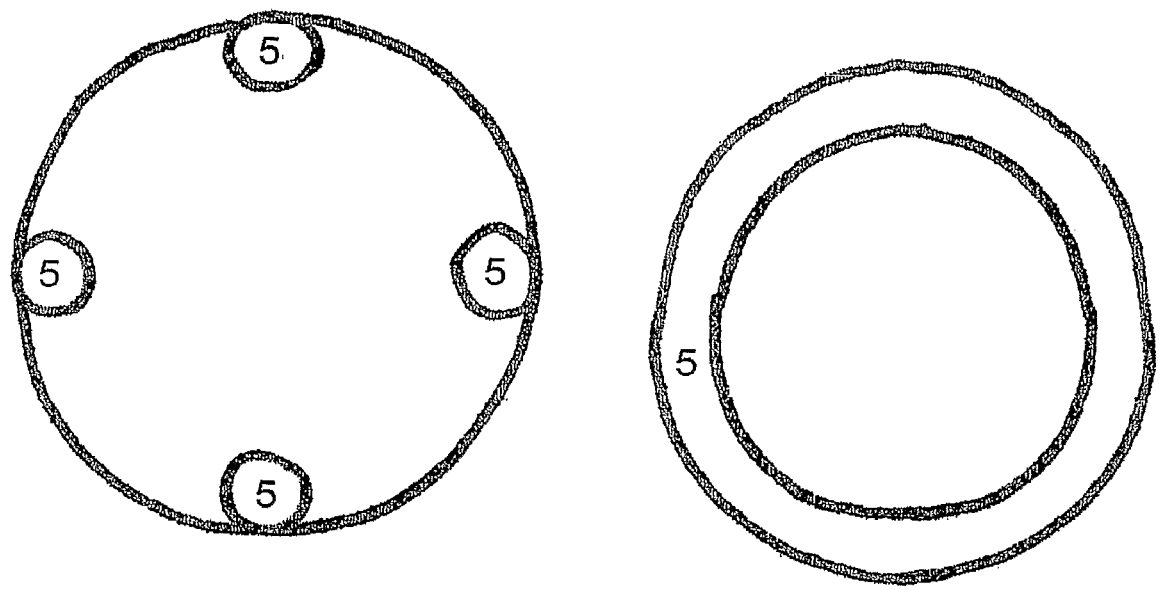
FIG. 6B shows two possible track patterns in the body of the gateway of the embodiment in FIG. 6A.

FIG. 6A shows a gateway where the steering part 5 is formed as a circular recess in the distal surface of the body 1 or holes placed in a circle. Two of the possible patterns of recesses are shown in FIG. 6B where the recesses forming the steering part 5 are shown from above.

Figure 7:
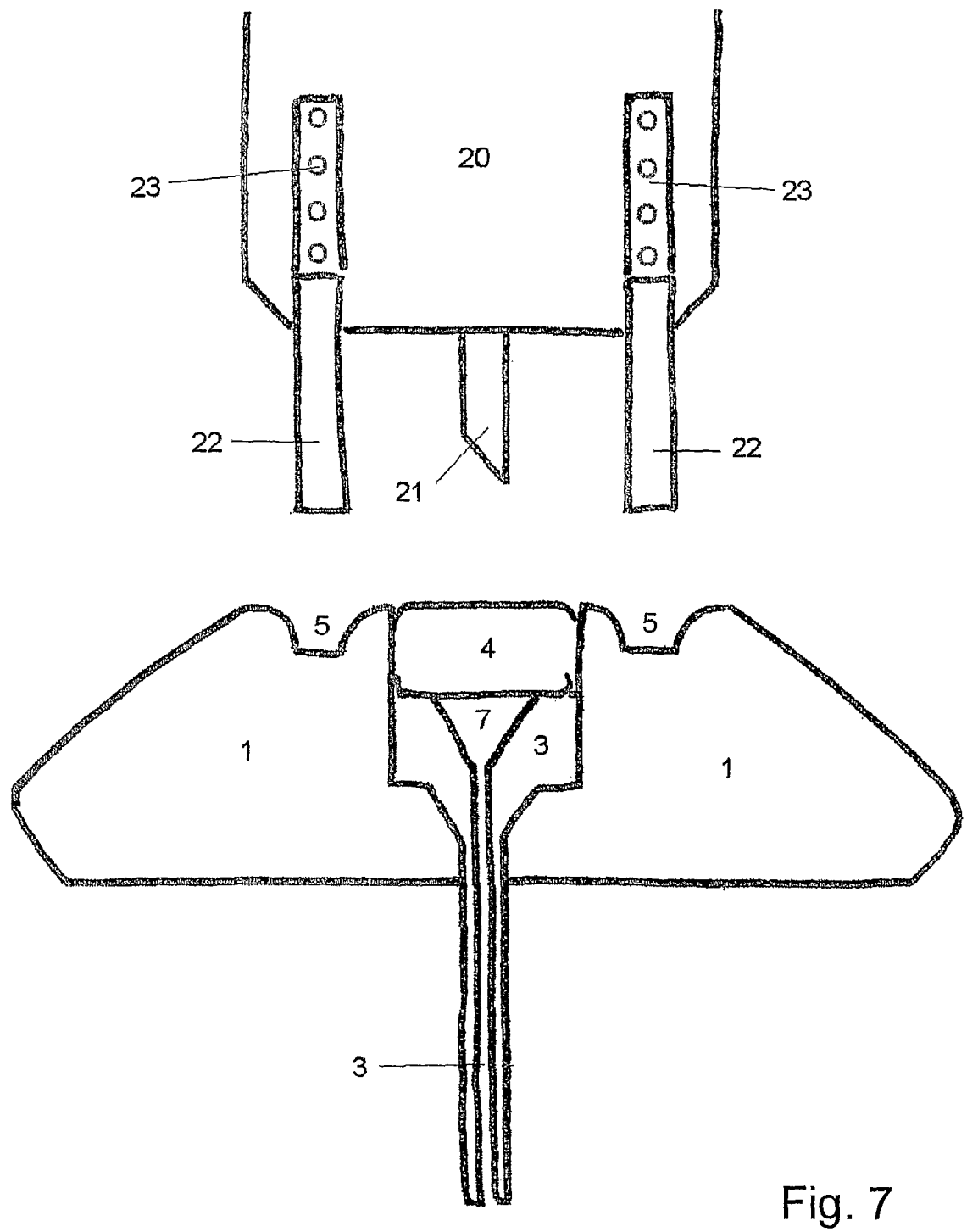
FIG. 7 shows a fourth embodiment of a gateway according to the invention where the gateway is provided with low tracks.

FIG. 7 shows yet another gateway where recesses of the steering part 5 are less deep and the protruding parts 22 of the needle unit 20 are influenced by one or more spring units 23. The spring units are pushing the protruding parts 22 down when they are in a relaxed position and are in this position protecting the surrounding from the needle 21. When the user wants to inject fluid into the gateway, the needle unit 20 with protruding parts 22 is placed in the steering part 5 and pushed down, this makes the projecting parts 22 disappear partly up in to the room where the spring units 23 are positioned. When pushed down the injection needle 21 extends beyond the projecting parts 22 and the needle 21 will penetrate the septum 4 and fluid is transferred to the cannula 3.

Figure 8:
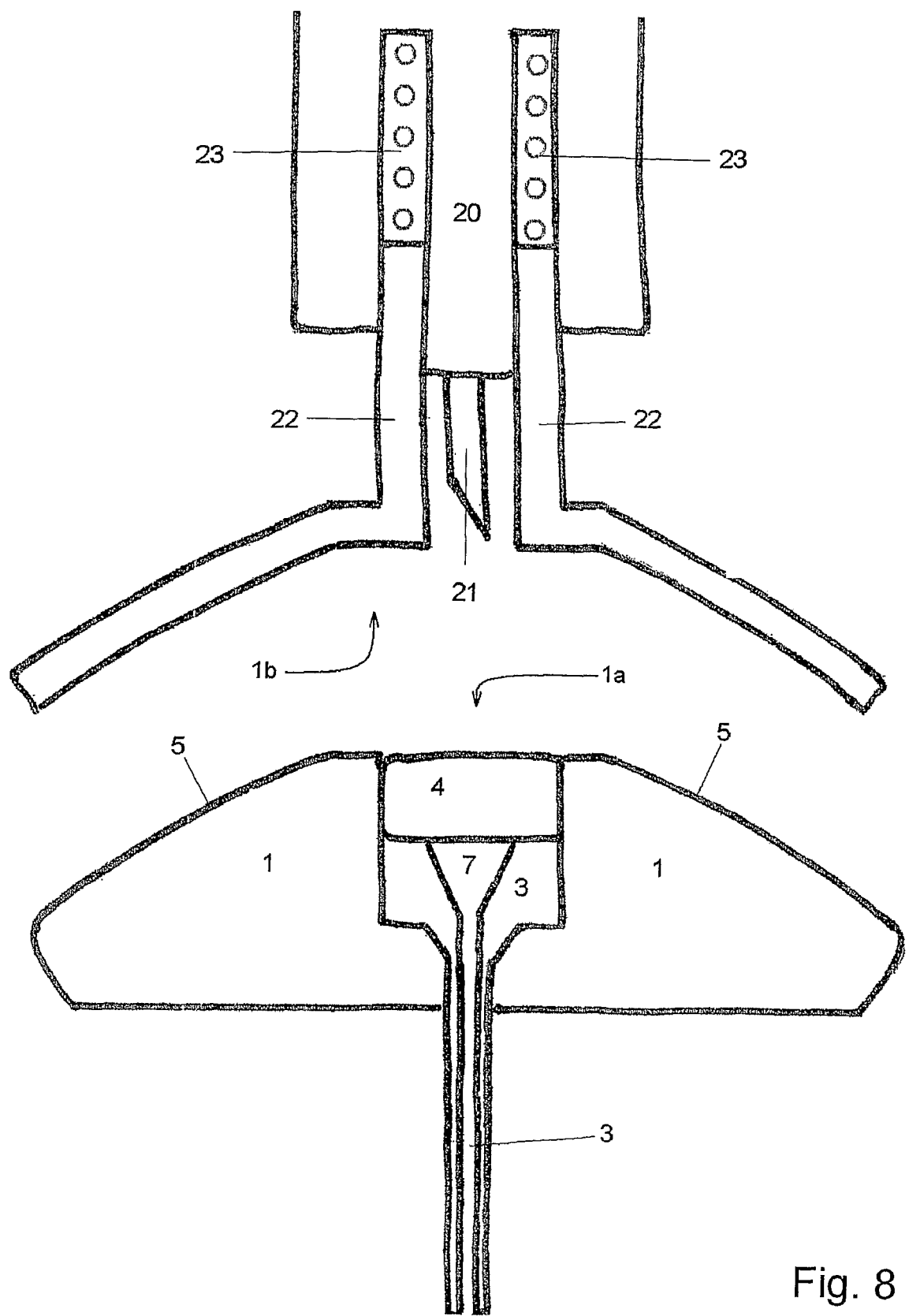
FIG. 8 shows a fifth embodiment of a gateway according to the invention where the surface of the body of the gateway is completely smooth.

FIG. 8 shows an embodiment of the gateway where the projecting parts 22 are formed as a cupola and the steering part 5 is the smooth distal surface of the body 1. This embodiment is also provided with springs 23 above the projecting parts 22. This makes the needle unit 20 more secure to handle before and after injection as there is no immediate access to the pointy needle 21.

Figure 9:
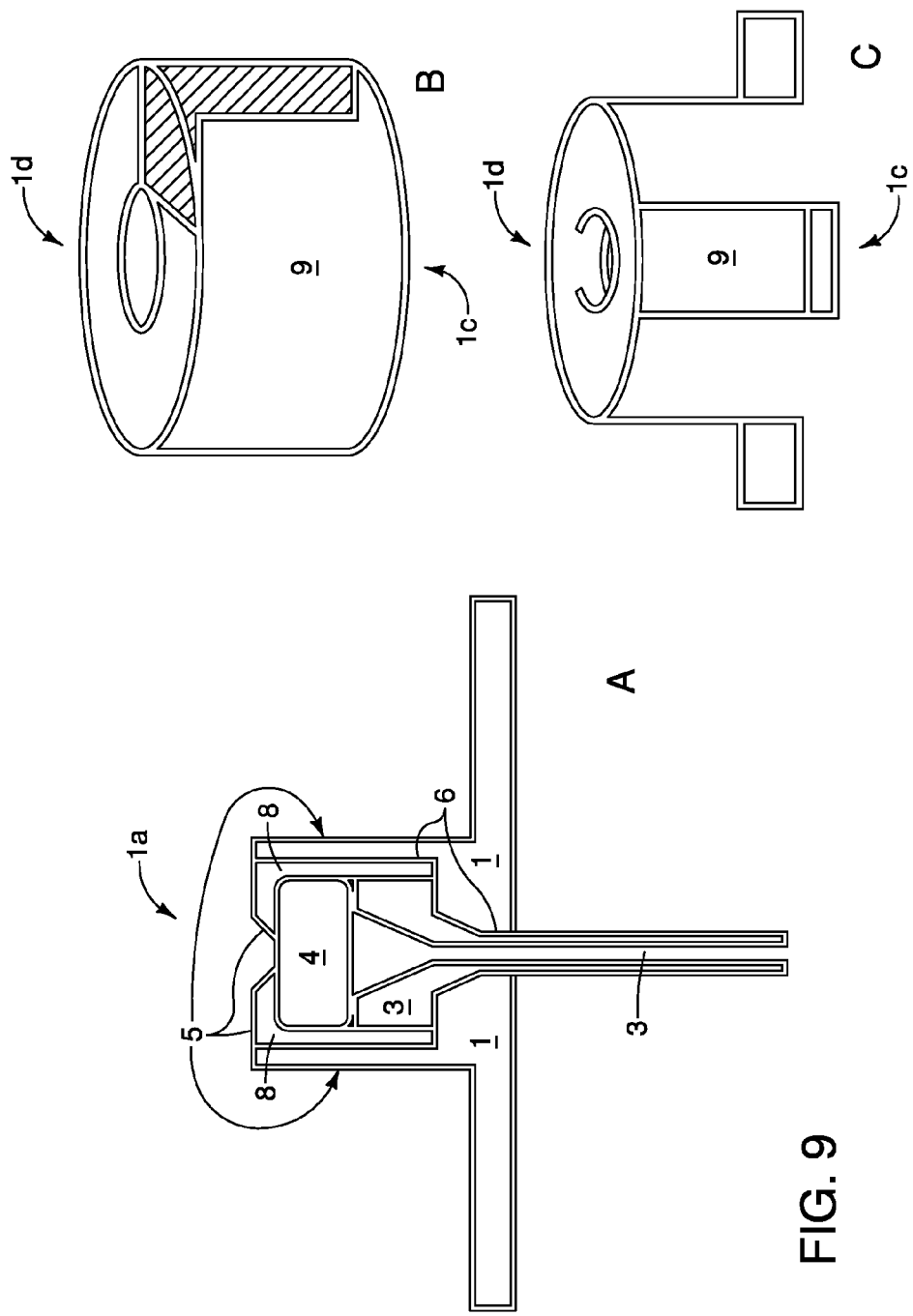
FIG. 9 shows a sixth embodiment of a gateway according to the invention where the gateway is provided with both internal and external steering parts.

FIG. 9A shows an embodiment where the steering part 5 is placed both inside the opening 6 and formed as the upright walls of the body 1. Also the steering part 5 is built of different components and possibly different materials as the form defining the steering part 5 is partly comprised by the surface of the upright walls of the distal surface of the body 1 and partly of the top surface of an internal element 8 which is placed inside the through-going opening 6.

FIGS. 9B and 9C show two round adapters or interfaces 9. These adapters 9 can be placed on top of the upright central part of the body 1 and can make it possible to use different kinds of needles or needle systems while still using the same gateway.

Figure 10:
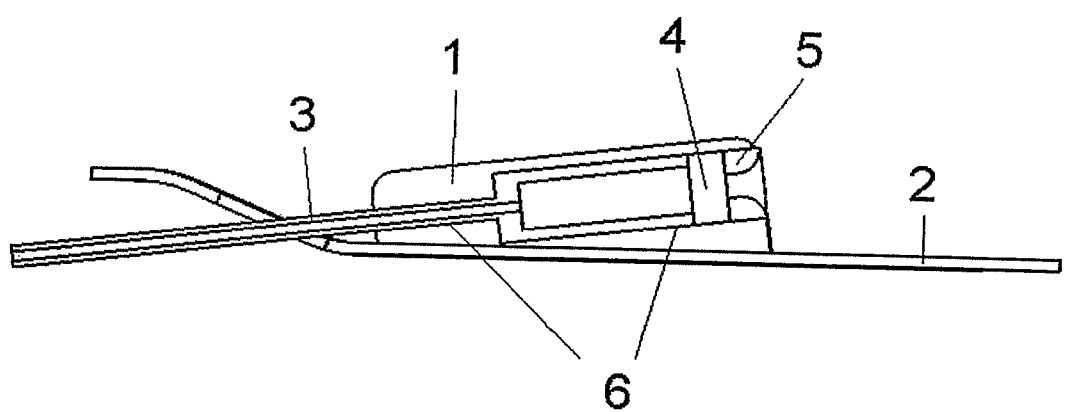
FIG. 10 shows a second embodiment of an inserter part according to the invention.

FIG. 10 shows yet another embodiment of a gateway. In this embodiment the through-going opening 6 of the body 1 is situated almost parallel to the skin of the patient when the gateway has been inserted. The gateway according to this embodiment can be injected in an angle from approximately 0°—or the angle in which the gateway is supposed to stay after insertion—to approximately 90°. No matter from which angle the gateway is injected, it is after injection laid down on the proximal side and secured to the skin by the mounting pad (2).

Figure 11:
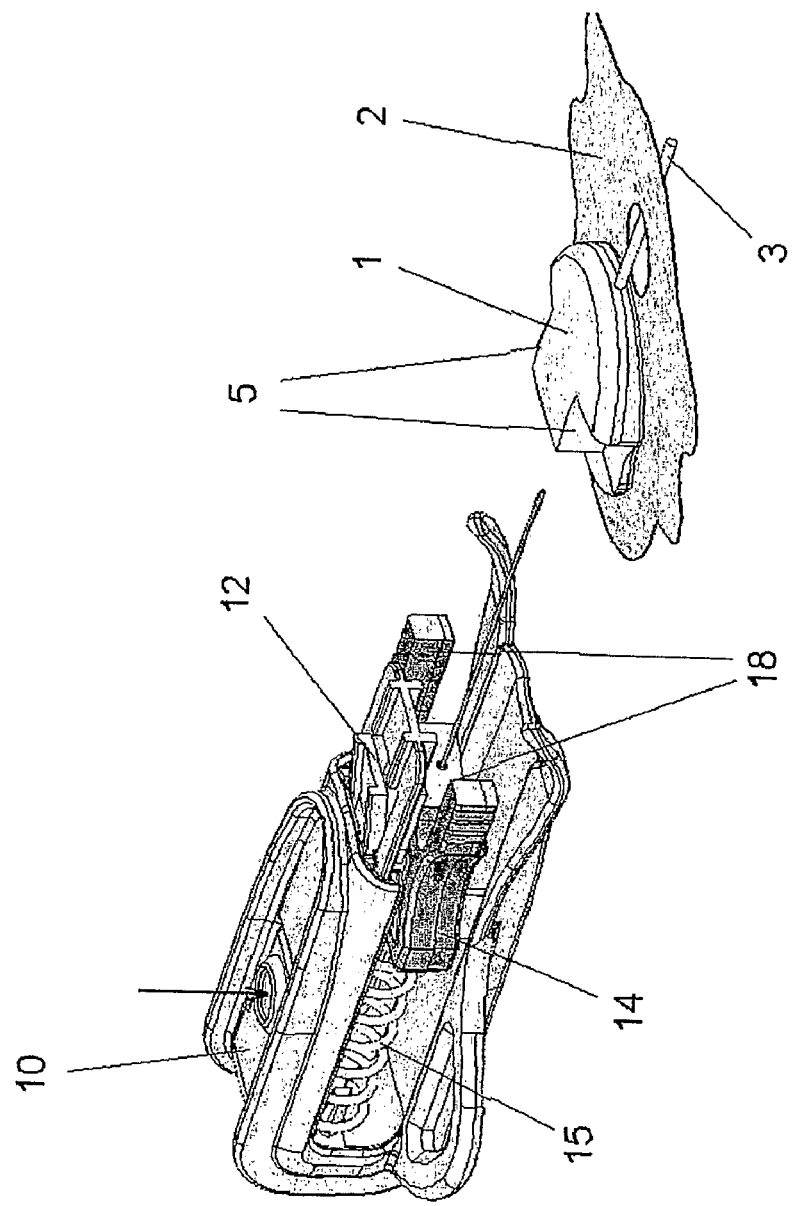
FIG. 11 shows an embodiment of an inserter for the gateway of FIG. 10.

FIG. 11 shows an embodiment of an inserter part adapted for the embodiment of the gateway shown in FIG. 10. This embodiment comprises a housing 10, a biasing unit 15 and a central part 14 which can slide between a forward and a retracted position. In FIG. 11 the central part 14 is in a forward position and the biasing unit 15 is relaxed. The central part 14 is provided with a detaining element 12, and when the central part 14 is in a retracted position where the biasing unit 15 is tightened, the detaining element 12 will rest against a protrusion on the internal side of the upper side of the housing 19 ("upper side" refers to the upper side of the housing 10 as seen in figure 11). Also the central part 14 is provided with means 18 for engaging the body 1 of the gateway.

Preferably the gateway system according to this embodiment is delivered to the user with the biasing unit 15 in a tightened state i.e. where the central part 14 is in a retracted position. When the user is going to insert the gateway, the user first remove a cover which has kept the gateway system sterile and then the user removes the release liner of the mounting pad 2, if the mounting pad 2 is covered by a release liner. Afterwards the user places the forward end of the inserter part against the skin in the desired insertion angle. The user then pushed the release means marked with and arrow in FIG. 11. The release means pushes down the detaining element 12 and releases the biasing unit 15. The central part 14 and the gateway is pushed forward where the penetrating needle penetrate the skin of the patient and inserts the cannula 3. After insertion of the cannula 3 the inserter part is removed from the gateway and the mounting pad 2 secured to the skin.

Figure 12A:
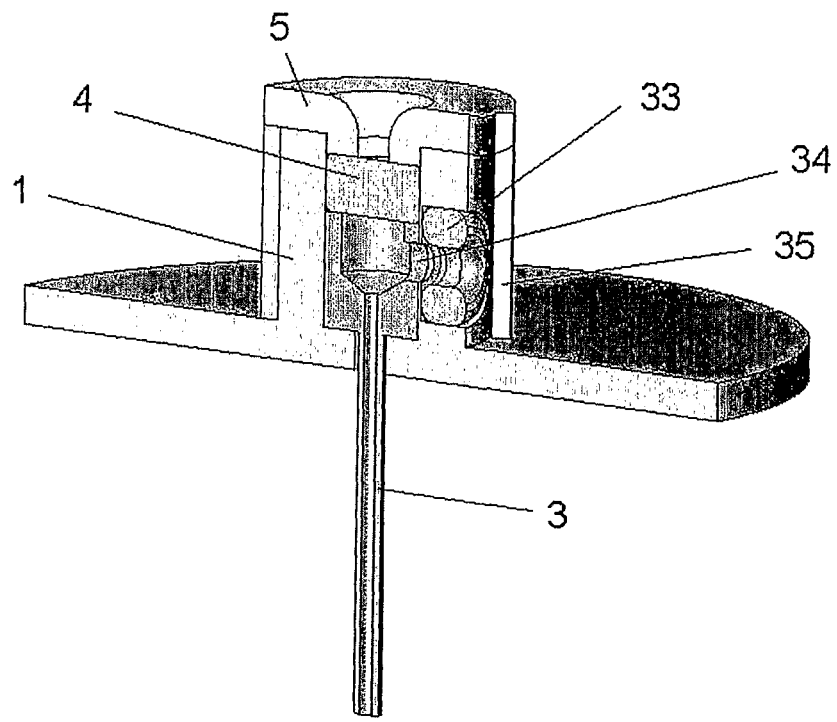
FIG. 12 shows an embodiment of an adaptor for a drug delivery device with no injection needle.
Figure 12B:
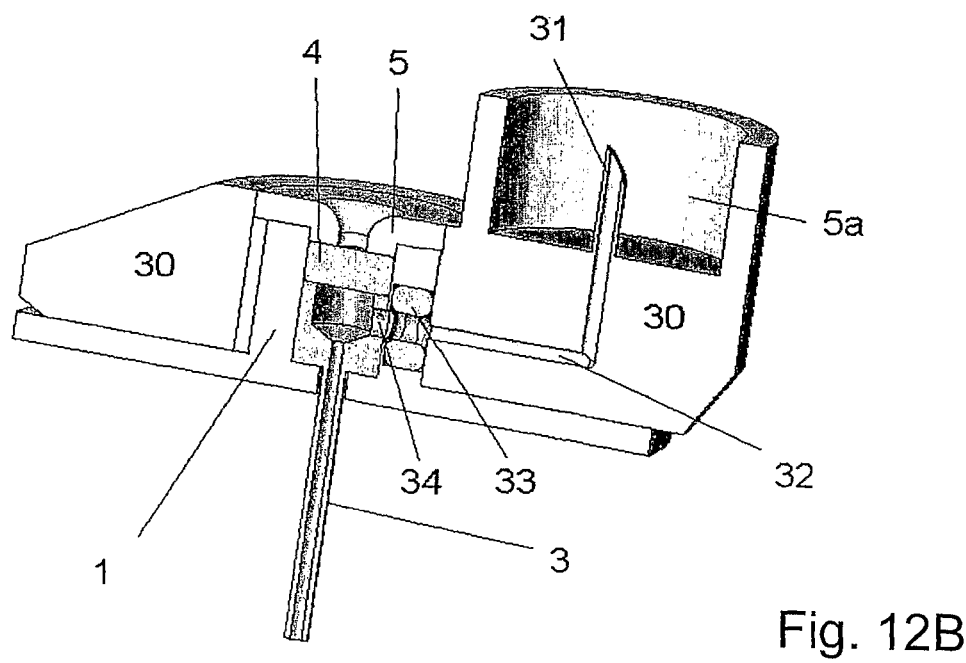

In FIGS. 12A and 12B is shown an embodiment of a gateway which has to possible injection positions: a first injection position is from the top where a drug delivery device as shown in FIG. 5 can be used, and a second injection position is through the wall forming the steering part 5.

In FIG. 12A the protecting cover of the gateway is removed and the gateway is ready for injection from the top. In FIG. 12B the cover is replaced with an adaptor which adaptor makes it possible to use a drug delivery device without an injection needle. The adaptor 30 comprises a steering part 5a with upright walls surrounding an upright needle 31 which can penetrate a septum in a drug delivery device. From the needle 31 the fluid medication flows through a pipe 32, the fluid passes an opening in the wall of the body of the gateway provided with a seal ring 33, and enters the cannula 3 through and opening 34 in the sidewall of the cannula 3. In order to assure correct position of the adaptor 30 the wall of the body of the gateway is provided with a recess of which a side wall 35 is shown in FIG. 12A.

Figure 13:
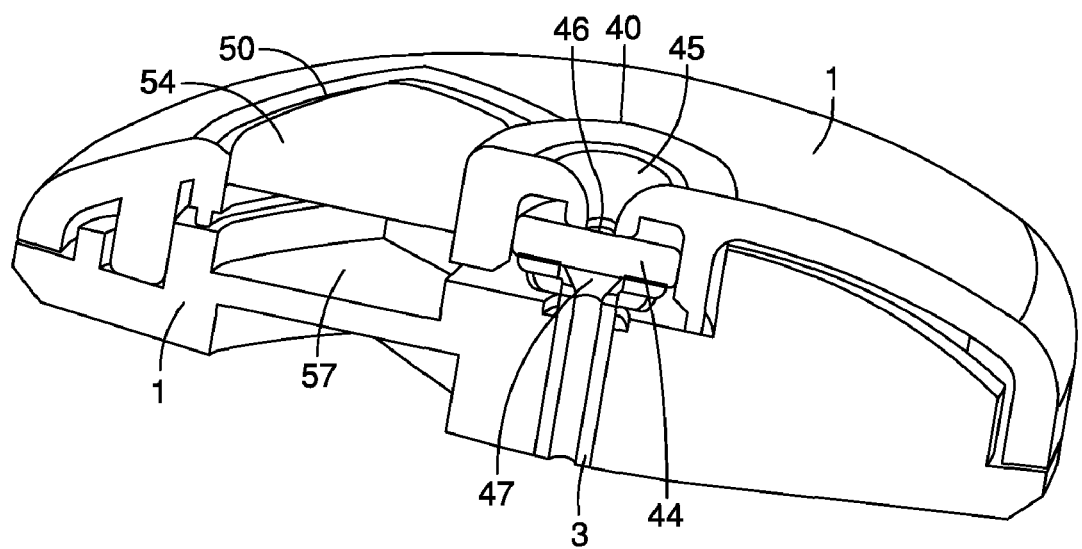
FIGS. 13 and 14 show an embodiment of the gateway according to the invention having two trough-going openings.
Figure 14:
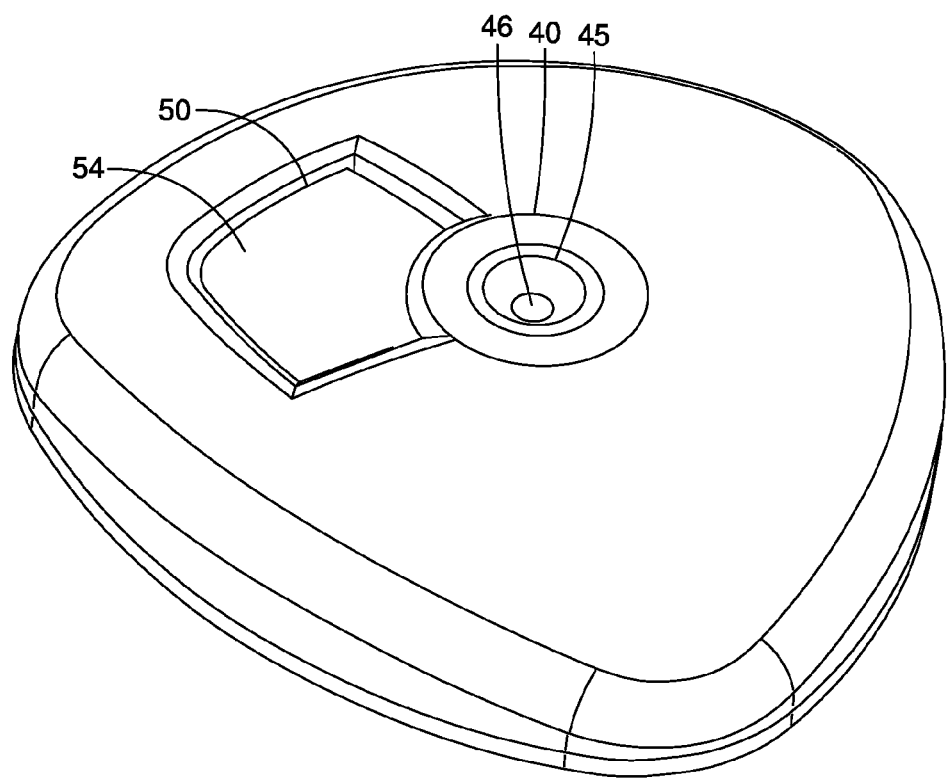

FIGS. 13 and 14 show an embodiment of a gateway which, like the embodiment of FIG. 12, has two possible injection positions: a first injection position 40 is positioned at the central top of the body 1 where a drug delivery device with a short pointy needle, normally max. 3 mm, can be used, and a second injection position 50 positioned at the peripheral top wall of the body 1 of the gateway where a drug delivery device with a long pointy needle, no maximum for the needle, can be used.

FIG. 13 shows the embodiment from above where the first injection position 40 is central and comprises relatively hard steering parts 45 surrounding the central opening 46. The second injection position 50 comprises a relatively large area of a septum 54 which can be penetrated by a pointy long needle in any position.

FIG. 14 shows a cut through the embodiment of FIG. 13. When fluid is injected through the first injection position 40 the short injection needle is inserted through the opening 46 and penetrates the septum 44 of the first injection position and the medication is injected into the cannula 3 and the room 47 below the septum 44. As the pointy needle used for injecting the medication is short the risque of penetrating the wall of the cannula 3 with the pointy needle is very small. When fluid is injected through the second injection position 50 the injection needle is inserted by penetrating the septum 54 of the second injection position and the medication fills the room 57 and flows through a passage into the cannula 3 below the septum 44. As the pointy needle used for injecting the medication, irrespective of where the septum 54 is penetrated, meets the hard material of the body 1 of the gateway when the needle is fully inserted, it does not matter how long the insertion needle is as the insertion length is defined by the depth of the room below the septum 54.

Figure 15:
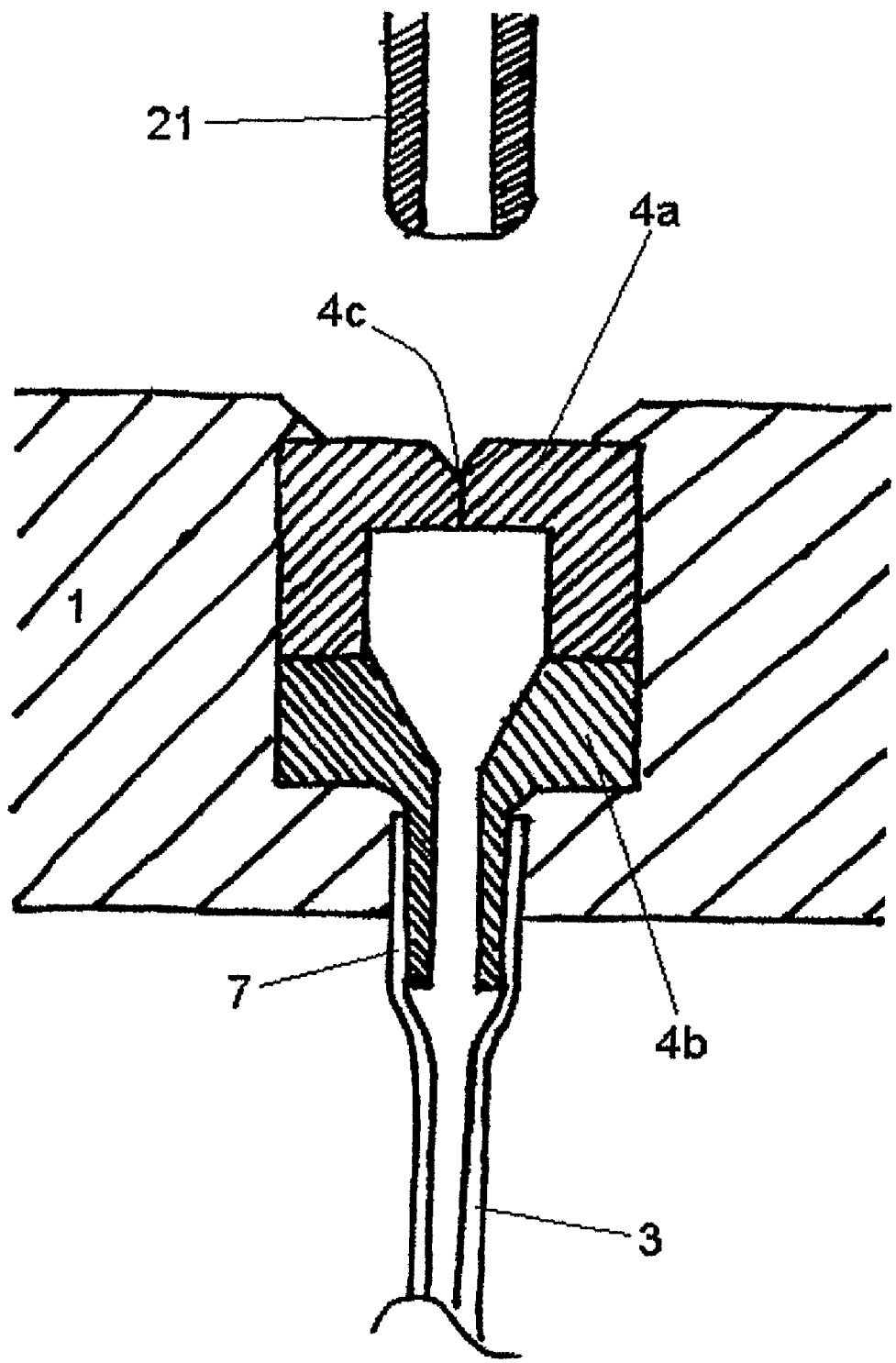
FIG. 15 shows an embodiment of the gateway having an entrance for a blunt needle.

FIG. 15 shows a cut through an embodiment of a gateway where the septum 4 is constructed of two sections, an upper section 4a and a lower section 4b, the two sections 4a and 4b might be molded as one coherent unit or it might be molded as to units which are fitted together in the through going opening formed in the body 1. In this embodiment a precut opening 4c is formed in the upper section 4a of the septum which makes it appropriate to use a blunt insertion needle 21 when delivering medication to the gateway. The precut slit is held in a closed position by compression as the septum 4 is press-fit into the body 1. When medication is to be delivered the blunt needle 21 of the delivery device is forced through the precut opening 4c until the blunt needle 21 meets the inclined walls of the lower section 4b of the septum, and then the drug is delivered into the cannula 3 area filling up at least part of the space inside the septum 4.

Figure 16:
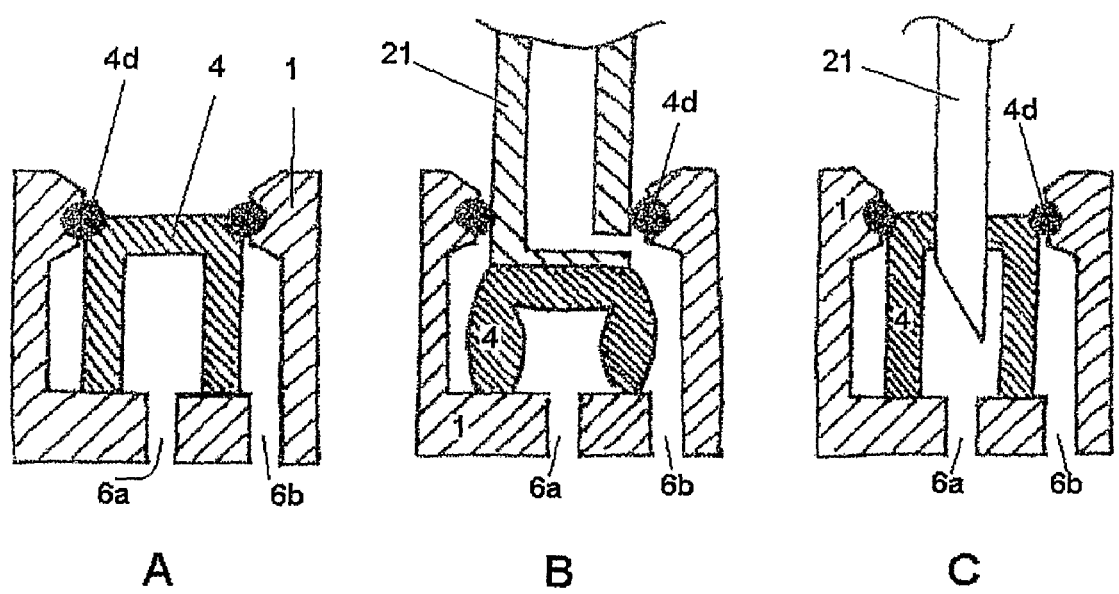
FIG. 16 shows another embodiment of the gateway according to the invention having two trough-going openings.

FIG. 16 shows a cut through an embodiment of a gateway where two different kinds of delivery devices can be used. FIG. 16 A shows the central part of a gateway with the cylindrical septum 4 which, together with an O-ring 4d, are blocking the through going opening of the body 1 which in this embodiment is split up into two passages for fluids 6a and 6b. The O-ring 4d is positioned in a circular groove formed in the body 1.

In FIG. 16 B it is shown how a blunt injection needle 21 can be used to deliver a drug to the gateway. This insertion needle 21 opens to the side and when pushed toward the septum 4 the insertion needle 21 compresses the septum 4 and cause a deformation of the septum. This deformation allows fluid to flow from the insertion needle 21 into the pass way 6b from where it can flow to the cannula (not shown). The O-ring 4d assures that no fluid passes between the injection needle 21 and the body 1 of the gateway while fluid is flowing out of the insertion needle 21.

In FIG. 16 C it is shown how a pointy injection needle 21 can be used to deliver a drug to the gateway. This insertion needle 21 opens at the pointy end and when pushed toward the septum 4 it penetrates the top of the septum and allow fluid to flow from the insertion needle 21 into the pass way 6a from where the medication can flow to the cannula (not shown). The O-ring 4d assures that fluid can not flow back between the septum 4 and the body 1 of the gateway while fluid is flowing out of the pointy insertion needle 21.

Figure 17:
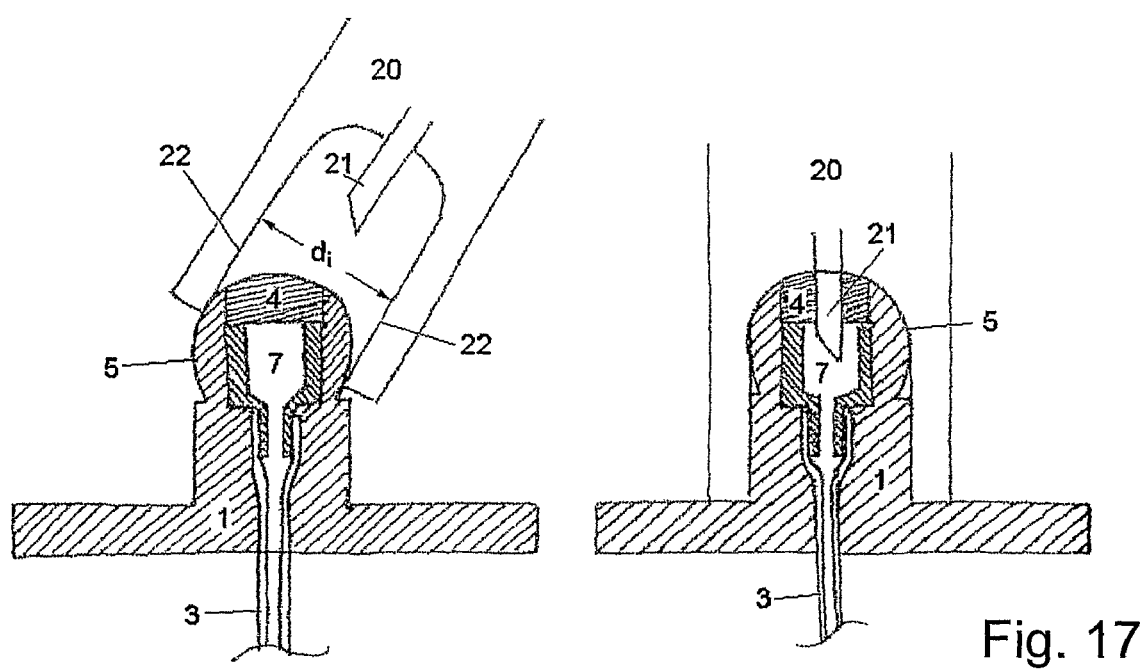
FIG. 17 shows an embodiment of the gateway where the cross-section of the top part of the entrance do not exceed $d_i$.

FIG. 17 shows an embodiment where the gateway is ready for injection of medication. The medication is injected with a syringe 20 provided with a pointy injection needle 21. In this embodiment the injection needle is retracted compared to the front part of the syringe. The front part of the syringe comprises one or more projecting parts 22, these parts protect the surroundings from the pointy needle before and after injection and correspond to the steering part 5. The correspondence between the steering part 5 and the projecting parts 22 assures easy and secure injection because it is only possible to place the injection needle in the correct position when the steering part 5 and the projecting parts 22 have to fit together. In this embodiment the steering part 5 provided by the body 1 and the septum 4 is partly formed as a sphere with a diameter corresponding closely to the inner distance $d_i$ between the projecting parts 22 of the injection device. This form allows the injection device 20 to be guided into correct position from any horizontal direction i.e. 360° around the body of the gateway although the injection device 20 diverts approximately up to 45° from vertical.

Figure 18:
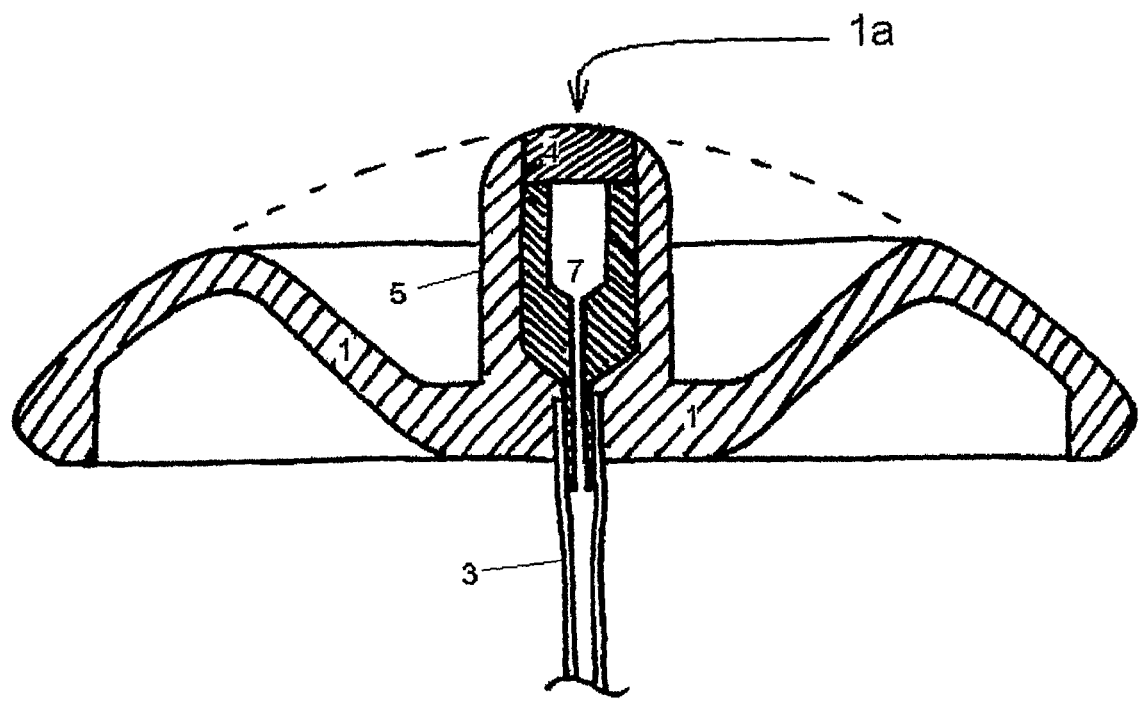
FIG. 18 shows an embodiment of the gateway where the cross-section of the top part of the entrance do not exceed $d_i$ which embodiment is also easy to keep clean.

FIG. 18 shows an embodiment of the gateway which is easy to keep clean and to clean while mounted on the skin of a patient. The body 1 of the gateway is formed with raised side parts which partly protect the raised center part and at the same time provide room for cleaning between the upright walls 5 and the raised sides of the body 1, also the edge between the upright walls 5 and the top provided by the septum 4 are rounded, preferably the top of the central part should be spherical.

Figure 19:
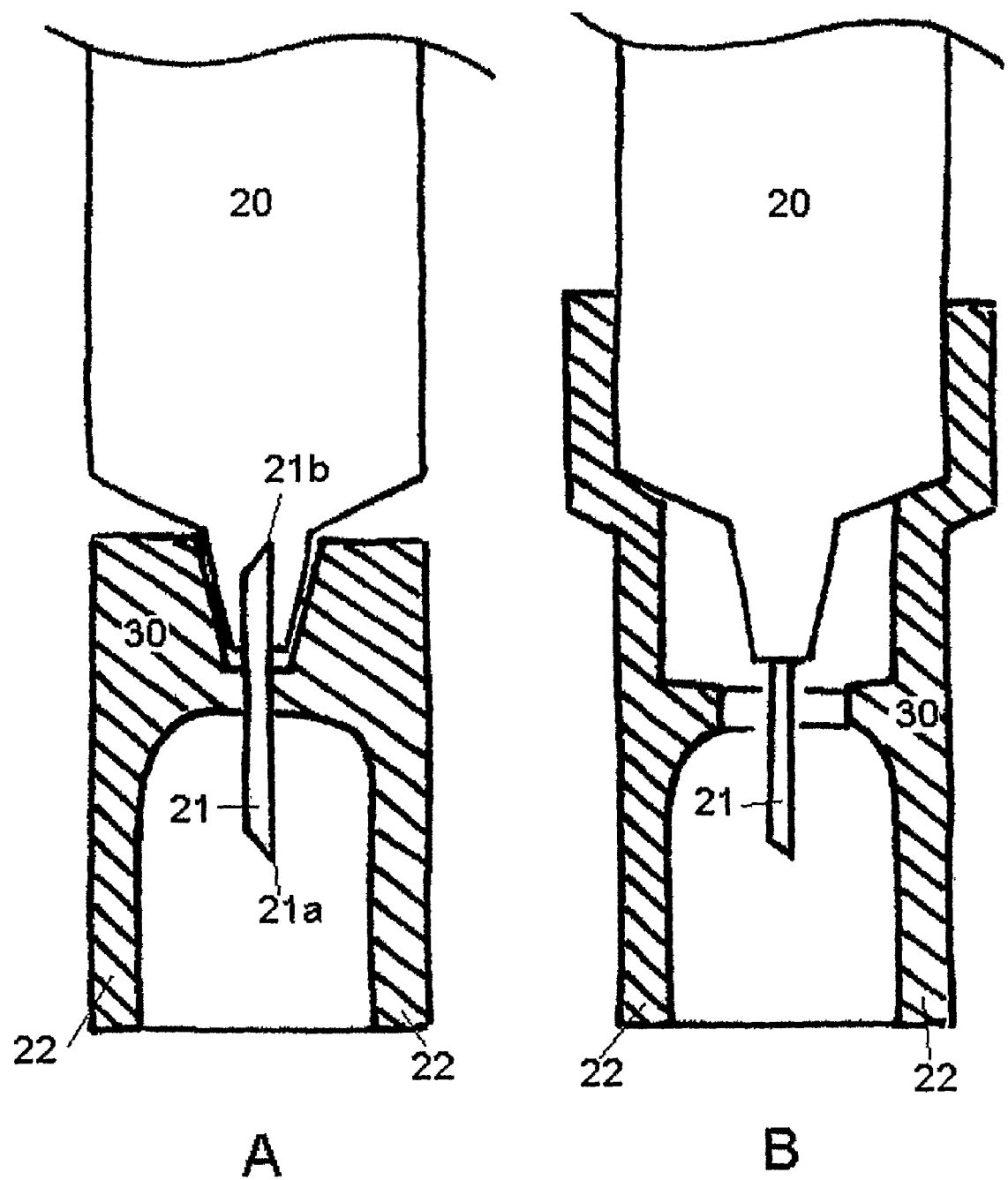
FIG. 19 shows two separate interfaces for positioning between the delivery device and the gateway.

FIGS. 19 A and B show two embodiments of adaptors 30, such an adaptor is intended for being positioned between the gateway and the delivery device. The first adaptor shown in FIG. 19 A has a pointy insertion needle 21 included, this insertion needle 21 is unreleasably fastened to the adaptor 30 and has a pointy proximal end 21a which end can penetrate a septum in a gateway (not shown) and a pointy distal end 21b which end can penetrate a septum in a delivery device 20. The second adaptor shown in FIG. 19 B does not have a pointy insertion needle 21 included, this adaptor 30 is used together with a delivery device 20 having a pointy insertion needle 21.

Figure 20:
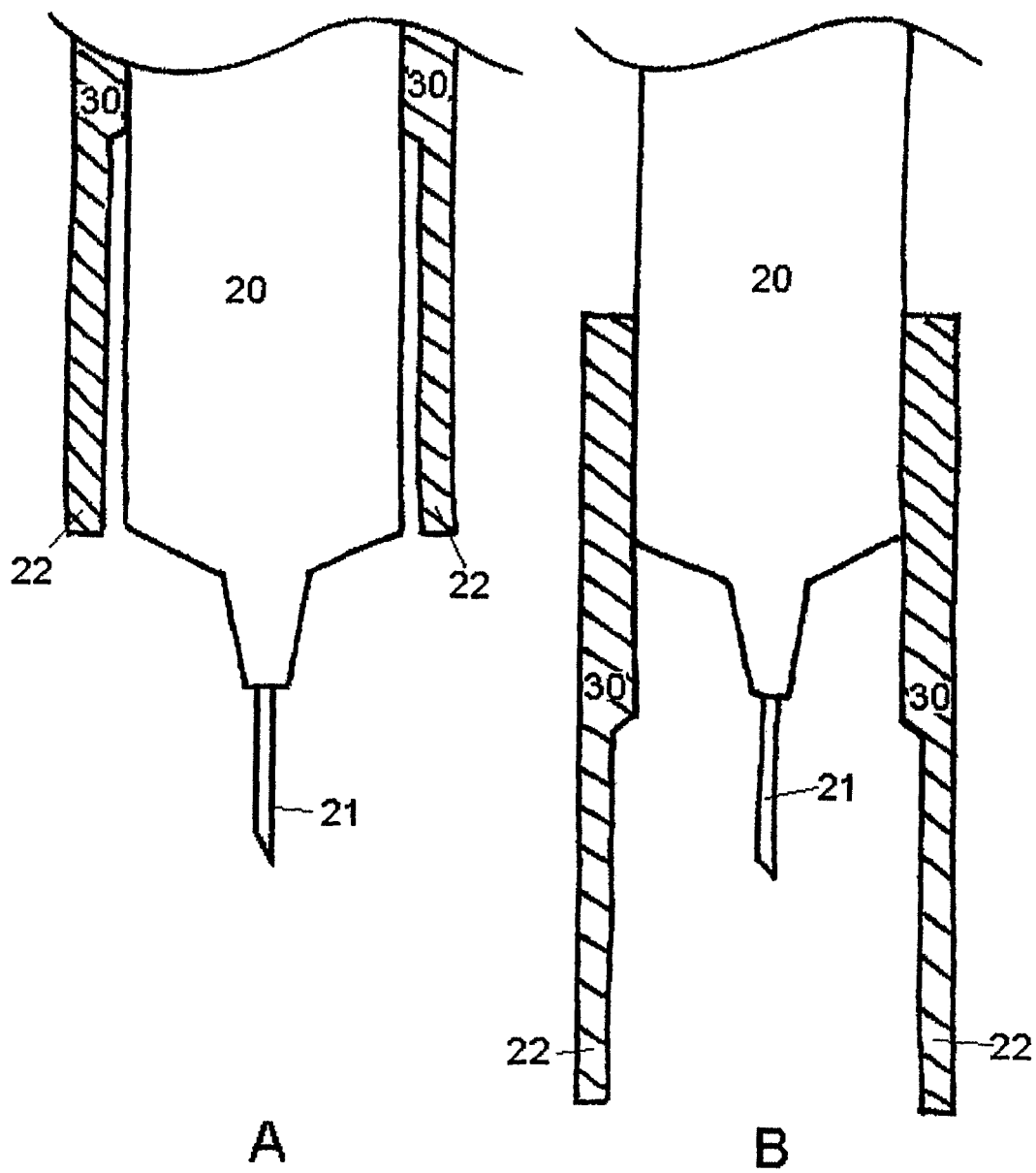
FIG. 20 shows an embodiment of an interface integrated with the delivery device which interface has two positions, A and B.

FIGS. 20 A and B show yet an embodiment of an adaptor 30. This embodiment of the adaptor 30 is fastened unreleasably to the delivery device 20 and the adaptor 30 has two secured positions, a retracted position as shown in FIG. 20 A and forward position as shown in FIG. 20 B. If the delivery device 20 is to be used to add medication to a standard gateway without steering parts 5 the adaptor 30 is in the retracted position of FIG. 20 A when transferring medication from the delivery device 20 to the gateway. If the delivery device 20 is to be used to add medication to a gateway with steering parts 5 as shown e.g. in FIG. 5 or 17 the adaptor 30 is in the forward position of FIG. 20 B when transferring medication from the delivery device 20 to the gateway.

Figure 21:
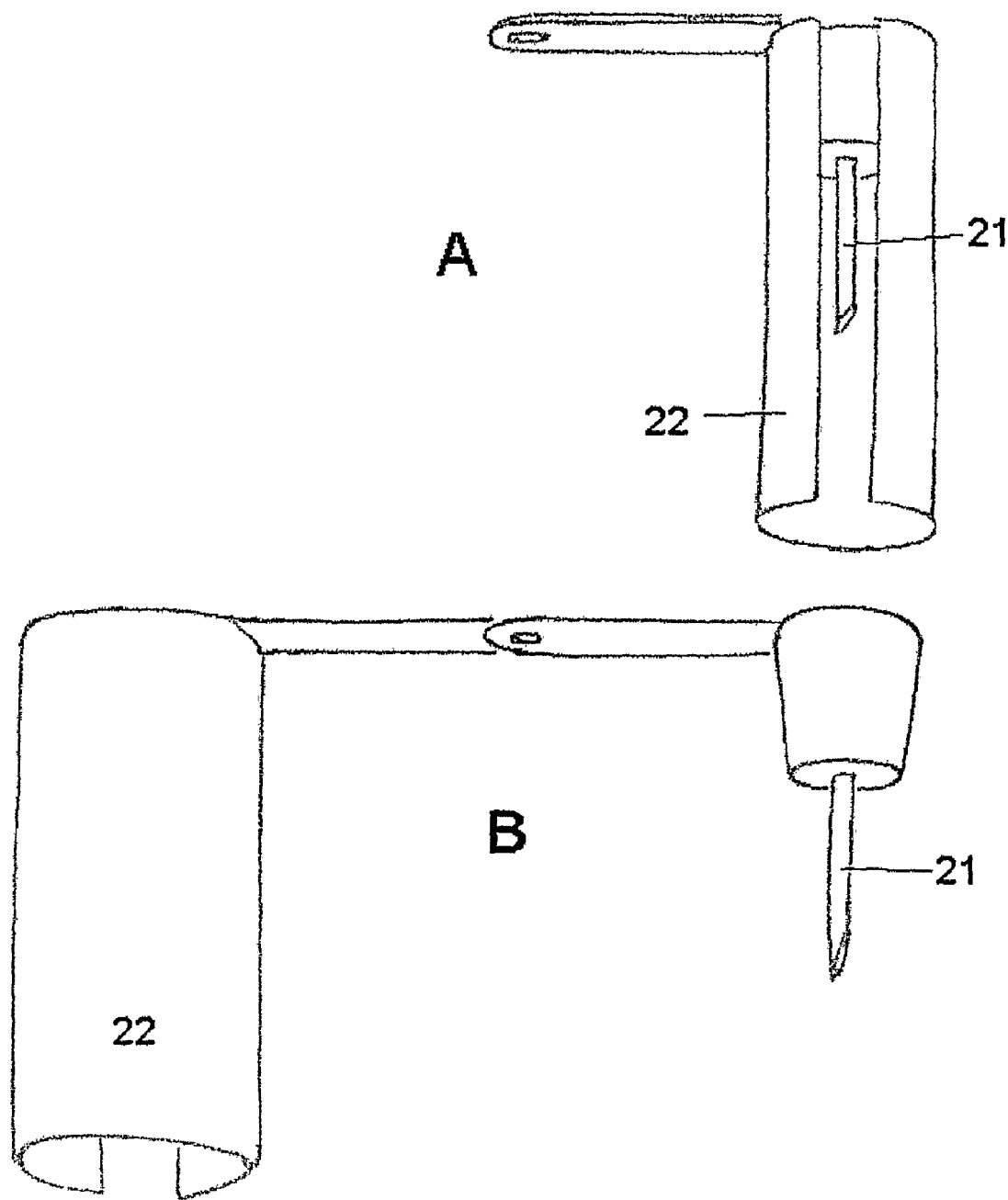
FIG. 21 shows another embodiment of an interface integrated with the delivery device which interface has two positions, A and B.

FIGS. 21 A and B show an embodiment of a retrofit needle with projecting parts 22. The projecting parts 22 has two positions, a central position shown in FIG. 21 A and a remote position shown in FIG. x7 B. The retrofit needle 21 is first mounted on the syringe in the normal position while the projecting parts 22 is in the remote position (B), then the syringe is filled with medication. After filling the syringe the projecting parts 22 are moved to the central position (A) covering the needle and the medication can be injected into a gateway with steering parts 5 as shown e.g. in FIG. 5 or 17.

Figure 22:
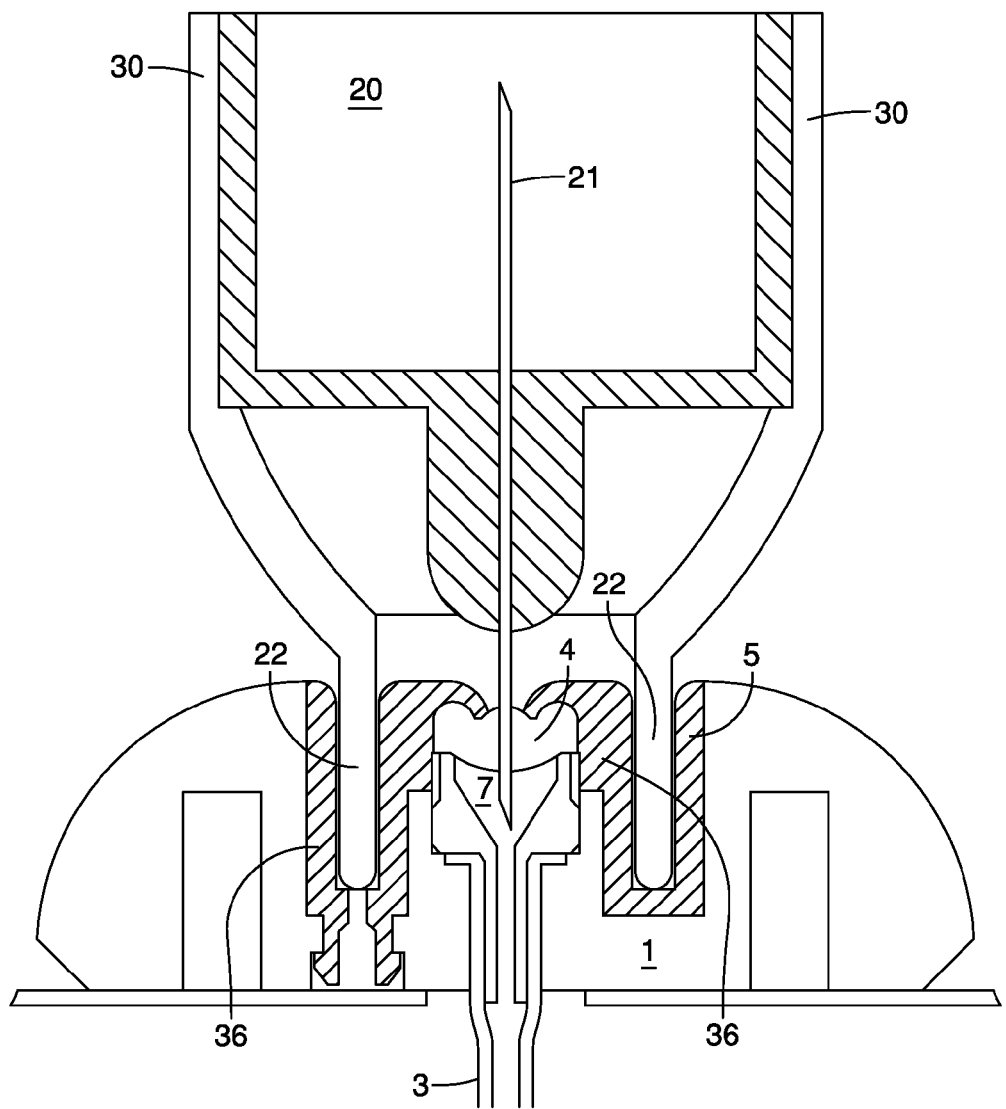
FIG. 22 shows an embodiment of a selected interface positioned between the delivery device and a selected socket 36 in the gateway.

FIG. 22 illustrates another embodiment of an adaptor 30. This embodiment of the adaptor 30 is intended to make a standard delivery device 20 fit with the body 1 of a gateway being equipped with removable steering parts 5 placed in a socket 36 in the body 1 of the gateway. The socket 36 is pushed into the body 1 before use and a click noise will verify correct positioning.

When transferring medication from a source, e.g. a vial containing medication, to the patient, the delivery device 20 is first filled from the not shown source and during the filling process the delivery device 20 is not protected by the adaptor. After filling the delivery device 20 the adaptor 30 is either positioned on the delivery device 20 or in the socket 36 formed by the removable steering parts 5. When transferring medication to the patient the delivery device 20 is inserted into the adaptor 30, when the delivery device 20 is inserted into the adaptor 30 the insertion needle 21 penetrates the protective septum 4 covering the entrance to the cannula 3 and medication can be injected into the space 7 above the cannula 3 and flow into the blood stream of the patient.

Figure 23:
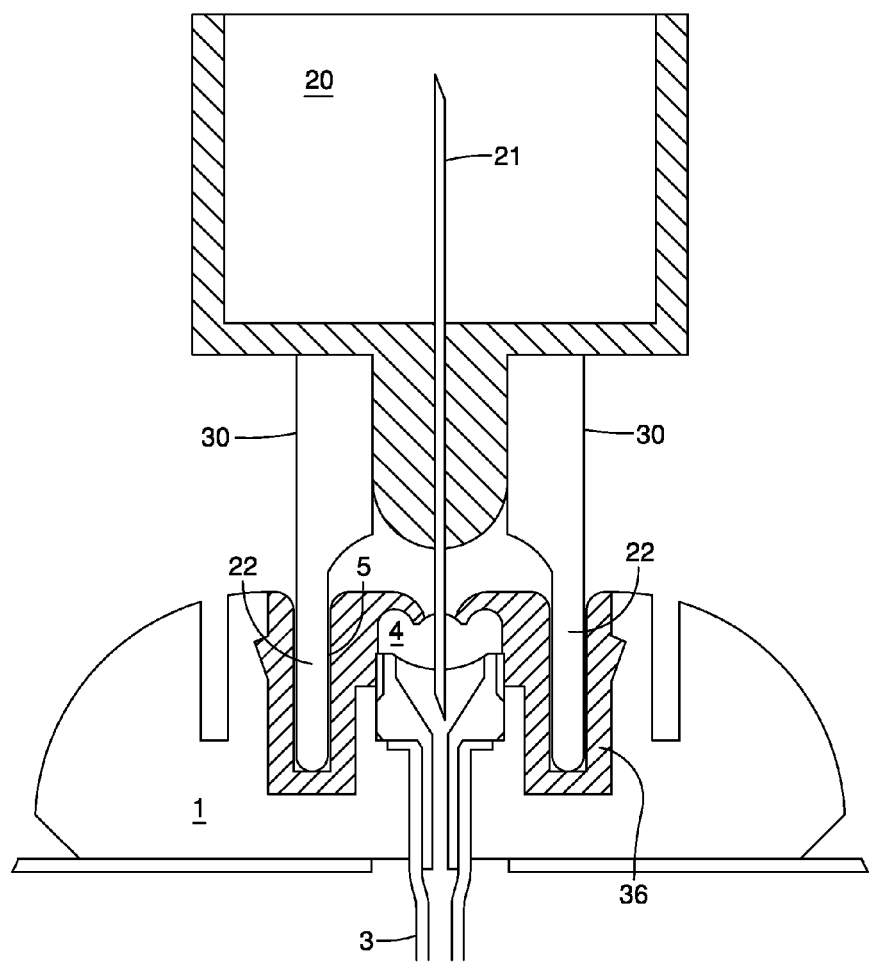
FIG. 23 shows another embodiment of a selected interface positioned between the delivery device and a selected socket 36 in the gateway.

FIG. 23 illustrates yet another embodiment of an adaptor 30. This embodiment of the adaptor 30 is also intended to make a standard delivery device 20 fit with the body 1 of a gateway being equipped with removable steering parts 5 placed in a socket 36 in the body 1 of the gateway.

This embodiment of the adaptor 30 has shorter arms adapting to the delivery device 20 compared to the embodiment of FIG. 22.

Figure 24:
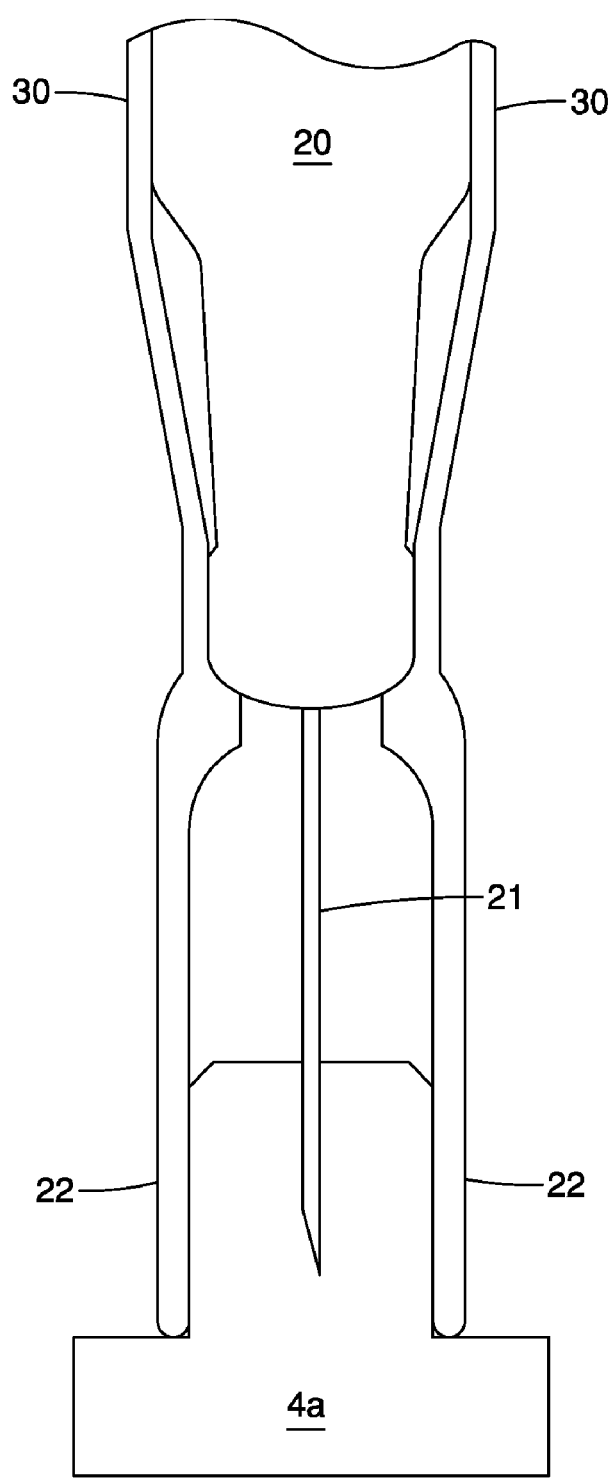
FIG. 24 shows an embodiment of an interface or adaptor used for a prefilled syringe.

FIG. 24 illustrates an embodiment of an adaptor 30 for a prefilled syringe. This embodiment of the adaptor 30 is placed in connection with a standard delivery device 20 before use. This system comprising a prefilled delivery device 20 is delivered to the user in the form illustrated in FIG. 24, that the delivery device 20 is prefilled means that the user does not have to fill the device 20 him/her self as the delivery device 20 including the drug is handed to the user in ready-to-use condition which includes that the drug is in a ready-to-use form and the needle section of the device is sterilized. When the user is going to inject medication with the prefilled delivery device 20, the cover 4a is first removed, then the delivery device 20 is positioned in or connected to the gateway or to another device ready for receiving medication and then the medication can be injected. Normally the delivery device 20 is a syringe.

The invention claimed is:

1. A system comprising:
   a gateway for subcutaneous injection of fluid, the gateway comprising a body with at least one through-going opening, at least one cannula and a restriction for microorganisms placed at a distal end of the at least one cannula or in the at least one through-going opening, the gateway having a proximal surface for contacting the patient's skin and a distal surface;
   an inserter device comprising a penetrating member and a biasing unit, the biasing unit adapted to urge the gateway from a retracted to a forward position when released;
   a drug delivery device, the drug delivery device configured for passing through the restriction of the gateway, and
   a separate interface comprising an interface proximal surface corresponding to the distal surface of the gateway and an interface distal surface corresponding to a proximal surface of the delivery device;
   wherein either the drug delivery device or the separate interface comprises an injection needle.

2. A system according to claim 1, wherein the distal surface of the gateway comprises a guide member.

3. A system according to claim 2, wherein the guide member comprises tracks formed as protruding or recessing elements relative to the distal surface.

4. A system according to claim 3, wherein the tracks comprise one or more recesses.

5. A system according to claim 3, wherein at least a portion of the guide member is separable from the body.

6. A system according to claim 5, wherein the guide member is formed in a separate socket wherein the socket is fastened to the body of the gateway before use.

7. A system according to claim 2, wherein a separable portion of the guide member is an adapter for the drug delivery device.

8. A system according to claim 6, wherein the interface comprises the injection needle.

9. A system according to claim 1, wherein the separate interface is secured to the delivery device.

10. A system according to claim 1, wherein the separate interface can be moved from a first position where the interface covers the injection needle to a second position where the injection needle is not covered.

11. A system according to claim 1, wherein the gateway comprises means for releasably connecting a sensor device for measuring the glucose content of the blood.

12. A system according to claim 1, wherein a portion of the inserter device in contact with the body of the gateway further comprises an end of an injection pen.

13. A system according to claim 1, further comprising a removable cover positionable on the distal surface of the body between injections.

14. A system according to claim 1, wherein the body comprises a transparent material.

15. A system comprising according to claim 9, wherein an end of the separate interface which is not secured to the drug delivery device comprises at least one cover configured for providing a protected and sterile environment around the insertion needle.

16. A system according to claim 15, wherein the drug delivery device is filled with a drug in a ready-to-use condition.

17. The system of claim 2 wherein the guide member comprises a material that is resistant to penetration by the penetrating member.

18. The system of claim 14 wherein the transparent material comprises acrylonitrile butadiene styrene (ABS), polypropylene (PP), polyethylene (PE) or combinations thereof.

19. The system of claim 1, wherein the drug delivery device further comprises the injection needle configured for passing through the restriction of the gateway.

* * * * *